(12) United States Patent
Wirtz et al.

(10) Patent No.: US 10,808,283 B2
(45) Date of Patent: Oct. 20, 2020

(54) METHODS AND KITS FOR THE MOLECULAR SUBTYPING OF TUMORS

(71) Applicants: BioNTech Diagnostics GmbH, Mainz (DE); Stratifyer Molecular Pathology GmbH, Cologne (DE)

(72) Inventors: Ralph Wirtz, Cologne (DE); Christoph Kneip, Berlin (DE)

(73) Assignees: BioNTech Diagnostics GmbH, Mainz (DE); STRATIFYER MOLECULAR PATHOLOGY GMBH, Cologne (DE)

( * ) Notice: Subject to any disclaimer, the term of this patent is extended or adjusted under 35 U.S.C. 154(b) by 387 days.

(21) Appl. No.: 14/912,813

(22) PCT Filed: Aug. 19, 2014

(86) PCT No.: PCT/EP2014/067675
§ 371 (c)(1),
(2) Date: Feb. 18, 2016

(87) PCT Pub. No.: WO2015/024942
PCT Pub. Date: Feb. 26, 2015

(65) Prior Publication Data
US 2016/0201137 A1 Jul. 14, 2016

(30) Foreign Application Priority Data
Aug. 19, 2013 (WO) .................. PCT/EP2013/002487

(51) Int. Cl.
C12Q 1/68 (2018.01)
C12Q 1/6886 (2018.01)

(52) U.S. Cl.
CPC ..... *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

FOREIGN PATENT DOCUMENTS

| EP | 2959021 B1 | 12/2015 |
|---|---|---|
| RU | 2008136193 A | 3/2010 |
| WO | WO-2007/092627 A2 | 8/2007 |
| WO | WO-2009/158143 | 12/2009 |
| WO | WO-2010/076322 | 7/2010 |
| WO | WO-2013/082440 | 6/2013 |
| WO | WO-2015/024942 A1 | 2/2015 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Perreard et al, Breast Cancer Research 8 (2) (Apr. 20, 2006).*
Ejlertsen et al, Annals of Oncology 23 (5), 1138 (May 2012).*
Lunardi et al, Breast Cancer Res. Treat. 137 (1), 167 (Jan. 2013).*
Cheang, et al., "Ki67 Index, HER2 Status, and Prognosis of Patients With Lumin B Breast Cancer", Journal of the National Cancer Institute, vol. 101, No. 10, May 20, 2009 (May 20, 2009), pp. 736-750.
Goldhirsch, et al., "Strategies for subtypes—dealing with the diversity of breast cancer: highlights of the St. Gallen international expert consensus on the primary therapy of early breast cancer 2011," Annals of Oncology, Jun. 27, 2011, vol. 2011, No. 22, pp. 1736-1747.
Laible, et al., "Technical validation of an RT-qPCR in vitro diagnostic test system for the determination of breast cancer molecular subtypes by quantification of ERBB2, ESR1, PGR and MKI67 mRNA levels from formalin-fixed paraffin-embedded breast tumor specimens.", BMC Cancer 2016, vol. 16, 2016 (14 pages).
Goldhirsch, A. et al., Personalizing the Treatment of Women with Early Breast Cancer: Highlights of the St Gallen International Expert Consensus on the Primary Therapy of Early Breast Cancer 2013. Ann Oncol. 2013; 24(9):2206-23.
Sinn, P. et al., Multigene Assays for Classification, Prognosis, and Prediction in Breast Cancer: a Critical Review on the Background and Clinical Utility. Geburtshilfe Frauenheilkd. 2013; 73(9):932-40.
Aigner et al., Molecular Subtyping on an mRNA Basis Predicts Therapeutic Response and Survival After Neoadjuvant Chemotherapy. Senologie—Zeitschrift für Mannadiagnostik und—Therapie 9-A2 (DOI: 10.1055/s-0032-1313368) (2012).
Communication Pursuant to Article 94(3) dated May 15, 2017 by the European Patent Office for European Patent Application No. 20140755642.7, which was published as EP2959021 on Dec. 30, 2015 (Inventor—Wirtz et al.; Applicant—Biontech Diagnostics GMBH) (5 pages).
Goldhirsch, et al., "Strategies for subtypes—dealing with the diversity of breast cancer: highlights of the St Gallen International Expert Consensus on the Primary Therapy of Early Breast Cancer 2011", (2011), Annals of Oncology, 22:1736-1747.
Joensuu, et al., "Adjuvant Docetaxel or Vinorelbine with or without Trastuzumab for Breast Cancer", (2006), N Engl J Med, 354:809-820.
Koutras, et al., "Evaluation of the prognostic and predictive value of HER family mRNA expression in high-risk early breast cancer: A Hellenic Cooperative Oncology Group (HeCOG) study", (2008), Brit. J. of Canc., 99:1775-1785.
Milde-Langosch, et al., "Validity of the proliferation markers Ki67, TOP2A, and RacGAPI in molecular subgroups of breast cancer", Breast Cancer Res Treat (2013) 137:57-67.
Pentheroudakis, et al., "Gene expression of estrogen receptor, progesterone receptor and microtubule-associated protein Tau in high-risk early breast cancer: a quest for molecular predictors of treatment benefit in the context of a Hellenic Cooperative Oncology Group trial", (2009), Breast Cancer Res Treat 2009, 116:131-143.

(Continued)

*Primary Examiner* — James Martinell
(74) *Attorney, Agent, or Firm* — Ballard Spahr LLP

(57) ABSTRACT

The present invention relates to an in vitro method of identifying a molecular subtype of a tumor in a cancer patient and to a method of stratifying a cancer patient for tumor treatment. The present invention further relates to kits that are useful for identifying a molecular subtype of a tumor in a cancer patient.

18 Claims, 23 Drawing Sheets
Specification includes a Sequence Listing.

(56) References Cited

OTHER PUBLICATIONS

Plirchopoulou, et al., "Prognostic significance of RACGAPI mRNA expression in high-risk early breast cancer: a study in primary tumors of breast cancer patients participating in a randomized Hellenic Cooperative Oncology Group trial", Cancer Chemother Pharmacol (2013) 71:245-255.
Skarlos, et al., "Triple-negative phenotype is of adverse prognostic value in patients treated with dose-dense sequential adjuvant chemotherapy: a translational research analysis in the context of a Hellenic Cooperative Oncology Group (HeCOG) randomized phase III trial", Cancer Chemother Pharmacol (2012) 69:533-546.
Sotiriou, et al., "Gene-Expression Signatures in Breast Cancer" (2009), N Engl J Med, 360(8):790-800.
Wang, et al., "A retrospective study of breast cancer subtypes: the risk of relapse and the relations with treatments", Breast Cancer Res Treat (2011) 130:489-498.
International Search Report dated Jan. 27, 2015 for international application PCT/EP2014/067675, filed on Aug. 19, 2014 and published as WO 2015/024942 on Feb. 26, 2015 (Applicant—Biontech Diagnostics GmbH // Inventor—Wirtz, et al.) (5 pages).
Written Opinion of the International Searching Authority dated Jan. 27, 2015 for international application PCT/EP2014/067675, filed on Aug. 19, 2014 and published as WO 2015/024942 on Feb. 26, 2015 (Applicant—Biontech Diagnostics GmbH // Inventor—Wirtz, et al.) (8 pages).
International Preliminary Report on Patentability of the International Searching Authority dated Feb. 23, 2015 for international application PCT/EP2014/067675, filed on Aug. 19, 2014 and published as WO 2015/024942 on Feb. 26, 2015 (Applicant—Biontech Diagnostics GmbH // Inventor—Wirtz, et al.) (10 pages).
Schepotin, I.B. et al., Molecular types of breast cancer, established on the basis of immunohistochemical markers: clinical and biological characteristics and prognosis. Klinicheskaja onkologija. 2012; 8(4):S1-4 (Abstract Provided). Abstract Only.
Database EMBL [Online] Mar. 3, 2009 (Mar. 3, 2009) "Genetic Alterations Useful for the Response Prediction of Malignant Neoplasia to Taxane-Based Medical Treatments", retrieved from EBI accession No. EM_PAT: DM024911.
Database EMBL [Online] Jun. 5, 2009 (Jun. 5, 2009), "Sequence 118359 from Patent W02005116265", retrieved from EBI accession No. EM_PAT: HA897174.
Database Geneseq [Online] Mar. 14, 2013 (Mar. 14, 2013), "Human Ki67 gene-specific quantitative PCR primer sense, SEQ 17.", retrieved from EBI accession No. GSN: BAJ91950.
Database Geneseq [Online] Mar. 14, 2013 (Mar. 14, 2013), "Human PGR gene quantitative RT-PCR reverse primer, SEQ: 72.", retrieved from EBI accession No. GSN: BAK14601.
Database Geneseq [Online] Dec. 28, 2007 (Dec. 28, 2007), "Human ERBB2 target sequence SEQ ID No. 18953.", retrieved from EBI accession No. GSN: AJV09444.
Database Geneseq [Online] Feb. 5, 2009 (Feb. 5, 2009) "Human estrogen receptor alpha real-time PCR primer, SEQ ID 25", retrieved from EBI accession No. GSN: AUL88348.
Database Geneseq [Online] Feb. 8, 2007 (Feb. 8, 2007), "Human estrogen alpha-receptor (ER-alpha)—targeted Taqman probe DNA.", retrieved from EBI accession No. GSN: AEM40664.
Database EMBL [Online] Oct. 28, 2010 (Oct. 28, 2010), "Predicting Response to a HER Dimerisation Inhibitor Based on Low HER3 Expression.", retrieved from EBI accession No. EM_PAT:FW417868.
Harris, L. et al., American Society of Clinical Oncology 2007 Update of Recommendations for the Use of Tumor Markers in Breast Cancer. J Clin Oncol. 2007; 25(33): 5287-312.
Paik, S. et al., A Multigene Assay to Predict Recurrence of Tamoxifen-Treated, Node-Negative Breast cancer. N Engl J Med. 2004; 351:2817-26.
Sahebjam, S. et al., Ki 67 is a Major, but Not the Sole Determinant of Oncotype Dx Recurrence Score. Br J Cancer. 2011; 105:1342-5.
Dietrich, W. et al., Testosterone Dependent Androgen Receptor Stabilization and Activation of cell Proliferation in Primary Human Myometrial Microvascular Endothelial Cells. 2011; Fertil Steril. 95(4):1247-55.e1-2.
Goncalves, R. and Bose, R., Using Multigene Tests to Select Treatment for Early-Stage Breast Cancer. J Natl Compr Canc Netw. 2013; 11(2):174-82.
NCBI, GenBank Accession No. FW417868.1, Predicting Response to a HER Dimerisation Inhibitor Based on Low HER3 Expression. 2010 (1 page).
Parker, J.S. et al., Supervised Risk Predictor of Breast Cancer Based on Intrinsic Subtypes. J Clin Oncol, 2009; 27(8):1160-7.
Schneeweiss, A. et al., A Randomized Phase II Trial of Doxorubicin Plus Pemetexed Followed by Docetaxel Versus Doxorubicin Plus Cyclophosphamide Followed by Docetaxel as Neoadjuvant Treatment of Early Breat Cancer. Ann Oncol. 2011; 22:609-17.
Von Minckwitz, G. and Fontanella, C., Selecting the Neoadjuvant Treatment by Molecular Subtype: How to Maximize the Benefit? Breast. 2013; 22(Suppl 2):S149-51.
Wirtz, R.M., "MammaTYPER: Ki67 mRNA Single Gene Measurement Predicts Response to Chemotherapy" Presentation. STRATIFYER. Info@stratifyer.de. (2012) (Original—16 Pages//Translation—8 pages).
Aigner, et al. "Ki-67 mRNA as a predictor for response to neoadjuvant chemotherapy in primary breast cancer", Cancer Research, Dec. 2012, vol. 72, No. 24 (Suppl.),(4 pages, Abstract).
PCT/EP2014/067675 (WO 2015/024942), dated Aug. 19, 2014, Biontech Diag. GmbH.

* cited by examiner

Time to event: Time to death (years)
Censored with death
Censor code 1
Grouped based on HER2, ESR1, PGR and Ki67 mRNA expression level Time to event: Time to distant recurrence (years)
Censored with distant recurrence
Censor code 1
Grouped based on HER2, ESR1, PGR and Ki67 mRNA expression level

Proportional Hazards Fit

Censored by Distant Recurrence

Whole Model

| | |
|---|---|
| Number of Events | 139 |
| Number of Censorings | 715 |
| Total Number | 854 |

| Model | -logLikelihood | ChiSquare | Degree of Freedom | Probability > ChiSquare |
|---|---|---|---|---|
| Difference | 25.9924 | 51.9847 | 8 | <0.001* |
| Full | 890.7213 | | | |
| Reduced | 916.7136 | | | |

Parameter Estimates

| Term | Estimates | Std. Error | Lower 95% Confidence | Upper 95% Confidence |
|---|---|---|---|---|
| ICH Subtype HER2 (Sotiriou et al.) | 0.130 | 0.182 | -0.236 | 0.478 |
| ICH Subtype LumA (Sotiriou et al.) | -0.440 | 0.173 | -0.787 | -0.106 |
| ICH Subtype LumB (Sotiriou et al.) | 0.126 | 0.184 | -0.247 | 0.476 |
| Present Invention Subtype HER2 | 0.131 | 0.193 | -0.247 | 0.510 |
| Present Invention Subtype LumA | -0.559 | 0.184 | -0.931 | -0.206 |
| Present Invention Subtype LumB | 0.274 | 0.159 | -0.046 | 0.580 |
| pT (Tumor Size) | 0.357 | 0.118 | 0.120 | 0.584 |
| pN (Nodal Status) | 0.246 | 0.082 | 0.056 | 0.365 |

Effect Likelihood Ratio Test

| Source | Number of Parameters | Degree of Freedom | L-R ChiSquare | Probability > ChiSquare |
|---|---|---|---|---|
| ICH (Sotiriou et al.) | 3 | 3 | 6.839 | 0.077 |
| Present Invention | 3 | 3 | 11.733 | 0.008* |
| pT (Tumor Size) | 1 | 1 | 8.537 | 0.004* |
| pN (Nodal Status) | 1 | 1 | 5.940 | 0.015* |

Figure 5

METHODS AND KITS FOR THE MOLECULAR SUBTYPING OF TUMORS

CROSS REFERENCE TO RELATED APPLICATION

The application is a National Phase Under 35 U.S.C. § 371 of International Application No. PCT/EP2014/067675 filed on Aug. 19, 2014, which claims the benefit of International Application Nos. PCT/EP2013/002487 filed on Aug. 19, 2013, the entire contents of which are herein incorporated by reference.

REFERENCE TO SEQUENCE LISTING

The Sequence Listing submitted Feb. 18, 2016 as a text file named "37592_0003U1_Sequence_Listing.txt" created on Jan. 7, 2016, and having a size of 4,077 bytes is hereby incorporated by reference pursuant to 37 C.F.R. § 1.52(e)(5).

TECHNICAL FIELD OF THE INVENTION

The present invention relates to an in vitro method of identifying a molecular subtype of a tumor in a cancer patient and to a method of stratifying a cancer patient for tumor treatment. The present invention further relates to kits that are useful for identifying a molecular subtype of a tumor in a cancer patient.

BACKGROUND OF THE INVENTION

Tumor prognosis and prediction of therapy response is closely related to the molecular subtype of the tumor. The current worldwide applied standard methodology for the detection of the receptor status of cancers, e.g., breast cancers, is immunohistochemistry (IHC) from formalin-fixed and paraffin-embedded (FFPE) biopsy or resection tissue. Currently, administration of endocrine or targeted systemic treatment (i.e. trastuzumab) is mostly based on IHC.

FFPE sample preparation and subsequent immunohistochemical staining with specific antibodies is a technology currently only performed in pathology laboratories. From microscopic examination of FFPE tumor tissues besides interpretation of staining results, pathologists derive further clinically essential information on tumor biology and tumor spread. Furthermore, the pathologist's interpretation of FFPE tissue examination can be considered an essential column in clinical decision making. In many countries pathologists are an integral part of the so-called case conference in breast cancer management decisions. Although IHC could easily be performed in centralized settings, personal opinion and experience of the examining pathologist is highly valued in the individual case decision.

However, several studies have demonstrated significant inter-observer variability and technical variability in up to 40% of immunohistochemistry results. Moreover, immunohistochemistry only allows a qualitative or, in some cases, a semi-quantitative statement regarding the respective receptor status.

Therefore, there is a need for a reliable, objective, quantitative and reproducible test system for the molecular subtyping of tumors, e.g. breast tumors, which facilitates the selection of suitable tumor treatment regimens (patient stratification), and allows prognosis and prediction of therapy success and assessment of a patient's risk for distant metastasis. Moreover, such test system should allow for decentralized testing that is suitable for a significant proportion of cancer patients.

SUMMARY OF THE INVENTION

In one aspect, the invention relates to an in vitro method of identifying a molecular subtype of a tumor in a cancer patient, said method comprising the steps:
  (a) determining the expression level of RNA transcript of human epidermal growth factor receptor 2 (HER2) in a sample of the tumor;
  (b) determining the expression level of RNA transcript of estrogen receptor (ESR1) in a sample of the tumor;
  (c) determining the expression level of RNA transcript of progesterone receptor (PGR) in a sample of the tumor; and
  (d) determining the expression level of RNA transcript of proliferation antigen Ki-67 (Ki67) in a sample of the tumor; and/or
  (e) determining the expression level of RNA transcript of RacGTPase-activating protein 1 (RACGAP1) in a sample of the tumor.

In one embodiment, determining the expression level of RNA transcript of HER2, ESR1, PGR and Ki67 and/or RACGAP1 comprises determining whether the expression level of RNA transcript of HER2, ESR1, PGR and Ki67 and/or RACGAP1 is lower or higher than a defined expression threshold of RNA transcript of HER2, ESR1, PGR and Ki67 and/or RACGAP1.

In one embodiment, step (a) is performed before steps (b), (c) and (d) and/or (e).

In one embodiment, step (d) and/or step (e) are performed after steps (a), (b) and (c).

In one embodiment, step (a) is performed before step (b), step (b) is performed before step (c), and step (c) is performed before step (d) and/or step (e).

In one embodiment, the molecular subtype is selected from the group comprising HER2-positive, triple-negative, luminal A and luminal B.

In one embodiment, an expression level of RNA transcript of HER2 which is higher than a defined expression threshold of RNA transcript of HER2 identifies the molecular subtype of the tumor as HER2-positive.

In one embodiment,
  an expression level of RNA transcript of HER2 which is lower than a defined expression threshold of RNA transcript of HER2;
  an expression level of RNA transcript of ESR1 which is lower than a defined expression threshold of RNA transcript of ESR1;
  an expression level of RNA transcript of PGR which is lower than a defined expression threshold of RNA transcript of PGR; and
  an expression level of RNA transcript of Ki67 which is lower or higher than a defined expression threshold of RNA transcript of Ki67
identify the molecular subtype of the tumor as triple-negative.

In one embodiment, the molecular subtype is luminal A or luminal B.

In one embodiment,
  an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is higher than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is higher than a defined expression threshold of RNA transcript of PGR; and an expression level of RNA transcript of Ki67 which is lower than a defined expression threshold of RNA transcript of Ki67 identify the molecular subtype of the tumor as luminal A.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is lower than a defined expression threshold of RNA transcript of PGR; and an expression level of RNA transcript of Ki67 which is lower or higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is lower than a defined expression threshold of RNA transcript of ESR1;

an expression level of RNA transcript of PGR which is higher than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is lower than a defined expression threshold of RNA transcript of ESR1;

an expression level of RNA transcript of PGR which is higher than a defined expression threshold of RNA transcript of PGR; and an expression level of RNA transcript of Ki67 which is lower than a defined expression threshold of RNA transcript of Ki67 identify the molecular subtype of the tumor as luminal A.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is lower than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, the molecular subtype luminal A is associated with a probability of distant recurrence-free survival 5 years after treatment which is at least 11%, preferably at least 13% higher than the probability of distant recurrence-free survival 5 years after treatment associated with molecular subtype luminal B and/or with a probability of survival 5 years after treatment which is at least 7%, preferably at least 9% higher than the probability of survival 5 years after treatment associated with molecular subtype luminal B.

In one embodiment, the method comprises step (d), and an expression level of RNA transcript of ESR1 which is higher than a defined expression threshold of RNA transcript of ESR1 and an expression level of RNA transcript of Ki67 which is higher than a defined expression threshold of RNA transcript of Ki67 indicates an increased risk of poor clinical outcome for the cancer patient, in particular an increased risk of distant metastasis.

In one embodiment, the method comprises step (e), and an expression level of RNA transcript of RACGAP1 which is higher than a defined expression threshold of RNA transcript of RACGAP1 indicates an increased risk of poor clinical outcome for the cancer patient.

In one embodiment, the method comprises steps (d) and (e), and an expression level of RNA transcript of Ki67 which is lower than a defined expression threshold of RNA transcript of Ki67 and an expression level of RNA transcript of RACGAP1 which is higher than a defined expression threshold of RNA transcript of RACGAP1 indicates an increased risk of poor clinical outcome for the cancer patient.

In one embodiment, the method comprises steps (d) and (e), and an expression level of RNA transcript of Ki67 which is higher than a defined expression threshold of RNA transcript of Ki67 and an expression level of RNA transcript of RACGAP1 which is higher than a defined expression threshold of RNA transcript of RACGAP1 indicates a her increased risk of poor clinical outcome for the cancer patient.

In one embodiment, poor clinical outcome comprises a relative reduction in or more of survival, recurrence-free survival and distant recurrence-free survival.

In one embodiment, the tumor is a solid tumor.

In one embodiment, the tumor is a breast tumor or is derived from a breast tumor.

In one embodiment, the cancer is breast cancer.

In one embodiment, the sample is RNA extracted from the tumor.

In one embodiment, the expression level of RNA transcript is determined by reverse transcription (RT) quantitative PCR.

In one embodiment, the quantitative PCR is fluorescence-based quantitative real-time PCR.

In one embodiment, the method comprises the use of ESR1-specific primers having a length of 15 to 30 nucleotides and comprising at least 10 contiguous nucleotides of the sequences of SEQ ID NOs: 1 and 2, and/or HER2-specific primers having a length of 15 to 30 nucleotides and comprising at least 10 contiguous nucleotides of the sequences of SEQ ID NOs: 4 and 5, and/or Ki67-specific primers having a length of 15 to 30 nucleotides and comprising at least 10 contiguous nucleotides of the sequences of SEQ ID NOs: 7 and 8, and/or PGR-specific primers having a length of 15 to 30 nucleotides and comprising at least 10 contiguous nucleotides of the sequences of SEQ ID NOs: 10 and 11, and/or CGAP1-specific primers having a length of 15 to 30 nucleotides and comprising at least 10 contiguous nucleotides of the sequences of SEQ ID NOs: 13 and 14.

In one embodiment, the method comprises the use of an ESR1-specific probe having a length of 20 to 35 nucleotides and comprising at least 15 contiguous nucleotides of the sequence of SEQ ID NO: 3, and/or a HER2-specific probe having a length of 20 to 35 nucleotides and comprising at least 15 contiguous nucleotides of the sequence of SEQ ID NO: 6, and/or a Ki67-specific probe having a length of 20 to 35 nucleotides and comprising at least 15 contiguous nucleotides of the sequence of SEQ ID NO: 9, and/or a PGR-specific probe having a length of 20 to 35 nucleotides and comprising at least 15 contiguous nucleotides of the sequence of SEQ ID NO: 12, and/or a RACGAP1-specific probe having a length of 20 to 35 nucleotides and comprising at least 15 contiguous nucleotides of the sequence of SEQ ID NO: 15.

In one embodiment, the expression level is normalized against the (mean) expression level of one or more reference genes in the sample of the tumor.

In one embodiment, the one or more reference genes are selected from the group comprising CALM2, B2M, RPL37A, GUSB, HPRT1 and GAPDH.

In a further aspect, the invention relates to a method of stratifying a cancer patient for tumor treatment, said method comprising, as a first step, identifying a molecular subtype of a tumor in the cancer patient using the in vitro method as defined above and, as a second step, selecting a tumor treatment regimen based on the molecular subtype identified by the in vitro method.

In one embodiment, the molecular subtype is selected from the group comprising HER2-positive, triple-negative, luminal A and luminal B.

In one embodiment,
the molecular subtype is HER2-positive, and the tumor treatment re en comprises administration of anti-HER2 antibodies and chemotherapeutic agents;
the molecular subtype is triple-negative, and the tumor treatment regimen comprises administration of chemotherapeutic agents;
the molecular subtype is luminal A, and the tumor treatment regimen comprises endocrine therapy; or
the molecular subtype is luminal B, and the tumor treatment regimen comprises endocrine therapy and, optionally, administration of chemotherapeutic agents.

In one embodiment, the molecular subtype is luminal B, and the tumor treatment regimen comprises administration of chemotherapeutic agents.

In one embodiment, the molecular subtype is luminal B, and the tumor treatment regimen comprises administration of a taxane, preferably docetaxel.

In one embodiment, the taxane is administered in combination with fluorouracil, epirubicin and cyclophosphamide (FEC).

In one embodiment, the tumor is a solid tumor.

In one embodiment, the tumor is a breast tumor or is derived from a breast tumor.

In one embodiment, the cancer is breast cancer.

In a further aspect, the present invention relates to a method of treatment of cancer, said method comprising, as a first step, stratifying a cancer patient for tumor treatment using the in vitro method as defined above, and, as a second step, providing the selected tumor treatment regimen to the cancer patient.

In a further aspect, the present invention relates to a kit useful for identifying a molecular subtype of a tumor in a cancer patient by means of reverse transcription (RT) quantitative PCR, said kit comprising:
at least one pair of HER2-specific primers and at least one HER2-specific probe;
at least one pair of ESR1-specific primers and at least one ESR1-specific probe;
at least one pair of PGR-specific primers and at least one PGR-specific probe; and
at least one pair of Ki67-specific primers and at least one Ki67-specific probe; and/or
at least one pair of RACGAP1-specific primers and at least one RACGAP1-specific probe.

In one embodiment, the quantitative PCR is fluorescence-based quantitative real-time PCR.

In one embodiment, detection of the probe is based on amplification-mediated probe displacement.

In one embodiment, the probe is a dual-label probe comprising a fluorescence reporter moiety and a fluorescence quencher moiety.

In one embodiment, the kit further comprises a reverse transcriptase and a DNA polymerase.

In one embodiment, the reverse transcriptase and the polymerase are provided in the form of an enzyme-mix which allows a one-step reverse transcription (RT) quantitative PCR.

In one embodiment, the kit further comprises at least one pair of reference gene-specific primers and at least one reference gene-specific probe.

In one embodiment, the reference gene is one or more selected from the group comprising CALM2, B2M, RPL37A, GUSB, HPRT1 and GAPDH.

In one embodiment, the kit further comprises at least one control RNA sample.

In one embodiment, the primers provide an amplicon size of less than 120 bp.

In one embodiment, the ESR1-specific primers have a length of 15 to 30 nucleotides and comprise at least 10 contiguous nucleotides of the sequences of SEQ ID NOs: 1 and 2, and/or the HER2-specific primers have a length of 15 to 30 nucleotides and comprise at least 10 contiguous nucleotides of the sequences of SEQ ID NOs: 4 and 5, and/or the Ki67-specific primers have a length of 15 to 30 nucleotides and comprise at least 10 contiguous nucleotides of the sequences of SEQ ID NOs: 7 and 8, and/or the PGR-specific primers have a length of 15 to 30 nucleotides and comprise at least 10 contiguous nucleotides of the sequences of SEQ ID NOs: 10 and 11, and/or the RACGAP1-specific primers have a length of 15 to 30 nucleotides and comprise at least 10 contiguous nucleotides of the sequences of SEQ ID NOs: 13 and 14.

In one embodiment, the ESR1-specific probe has a length of 20 to 35 nucleotides and comprises at least 15 contiguous nucleotides of the sequence of SEQ ID NO: 3, and/or the HER2-specific probe has a length of 20 to 35 nucleotides and comprises at least 15 contiguous nucleotides of the sequence of SEQ ID NO: 6, and/or the Ki67-specific probe has a length of 20 to 35 nucleotides and comprises at least 15 contiguous nucleotides of the sequence of SEQ ID NO: 9, and/or the PGR-specific probe has a length of 20 to 35 nucleotides and comprises at least 15 contiguous nucleotides of the sequence of SEQ ID NO: 12, and/or the RACGAP1-specific probe has a length of 20 to 35 nucleotides and comprises at least 15 contiguous nucleotides of the sequence of SEQ ID NO: 15.

In one embodiment, the tumor is a solid tumor.

In one embodiment, the tumor is a breast tumor or is derived from a breast tumor.

In one embodiment, the cancer is breast cancer.

In another aspect, the present invention relates to the use of a kit as defined above for identifying a molecular subtype of a tumor in a cancer patient.

In another aspect, the present invention relates to the use of a kit as defined above for assessing a cancer patient's risk for distant metastasis.

BRIEF DESCRIPTION OF THE FIGURES

FIG. 5 depicts a multivariate Cox regression analysis of DMFS comparing molecular subtyping by immunohistochemistry (Sotiriou et al. (2009), N Engl J Med, 360(8): 790-800) with molecular subtyping using the method in accordance with the present invention, based on the mRNA expression levels of HER2, ESR1, PGR and Ki67. The analysis clearly shows the superiority of the method of the present invention, as the immunohistochemical subtyping looses its significance when the results obtained by the method of the present invention are included in the Cox proportional hazards model.

Similar results are shown for tumors subtyped by IHC (86% vs. 89%, HR 1.175; CI 0.518-2.663).

Figure 15:
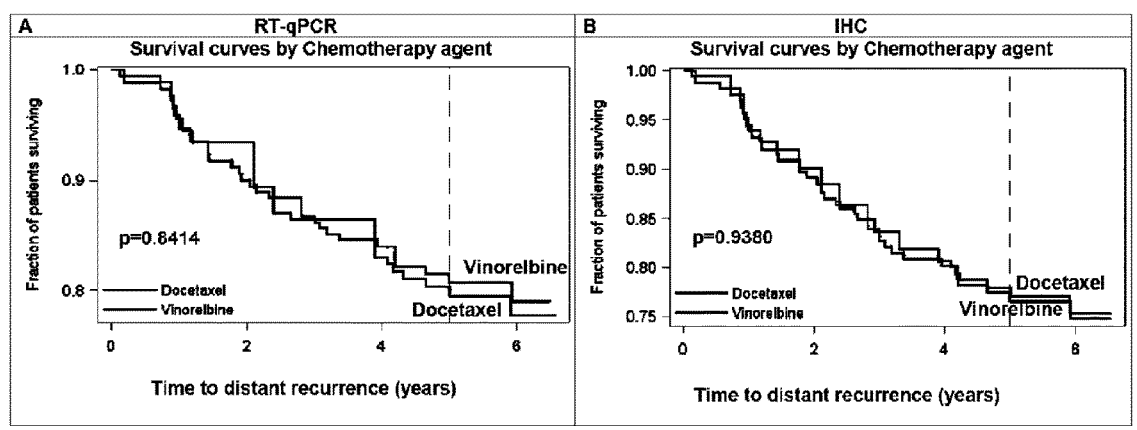

FIG. 15 depicts a Kaplan Meier analysis of distant metastasis free survival of HER2-positive tumors. A: When defined by the method of the present invention, HER2-positive patients do not differ in distant metastasis free survival when treated with docetaxel as compared to vinorelbine (80 vs. 81%, HR 1.070; CI 0.551-2.076). B: Similarly, when defined by IHC, differently treated HER2-positive patients do not show differences in survival (78% vs. 77%, HR 0.975; CI 0.516-1.843).

Figure 16:
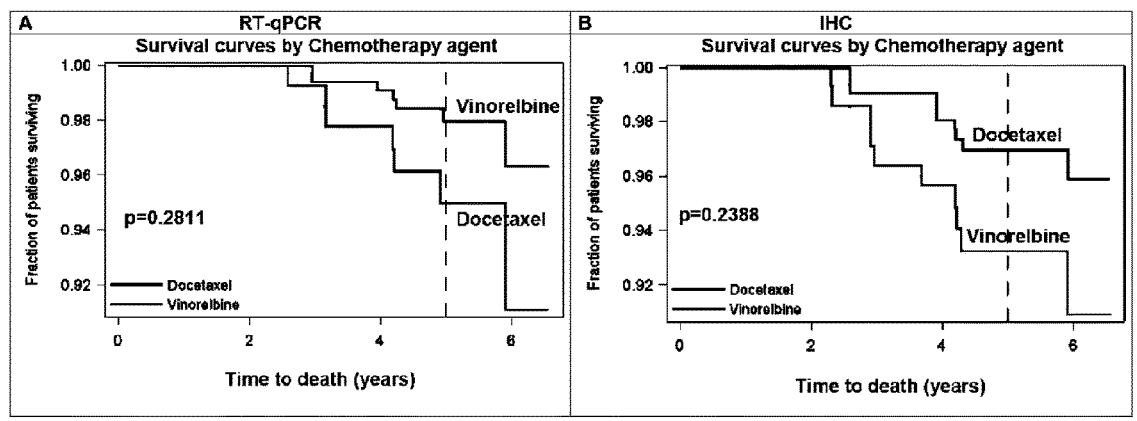

FIG. 16 depicts a Kaplan Meier analysis of overall survival of luminal A tumors. A: When defined by RT-qPCR, luminal A patients tend to have inferior overall survival rates when treated with docetaxel as compared to vinorelbine (95% vs. 98%, HR 2.471; CI 0.477-12.809). B: By contrast, when defined by IHC, luminal A patients show a weak, yet non-significant trend towards longer overall survival (97 vs. 93% HR 0.443; CI 0.114-1.716) when treated with docetaxel as compared to vinorelbine.

Figure 17:
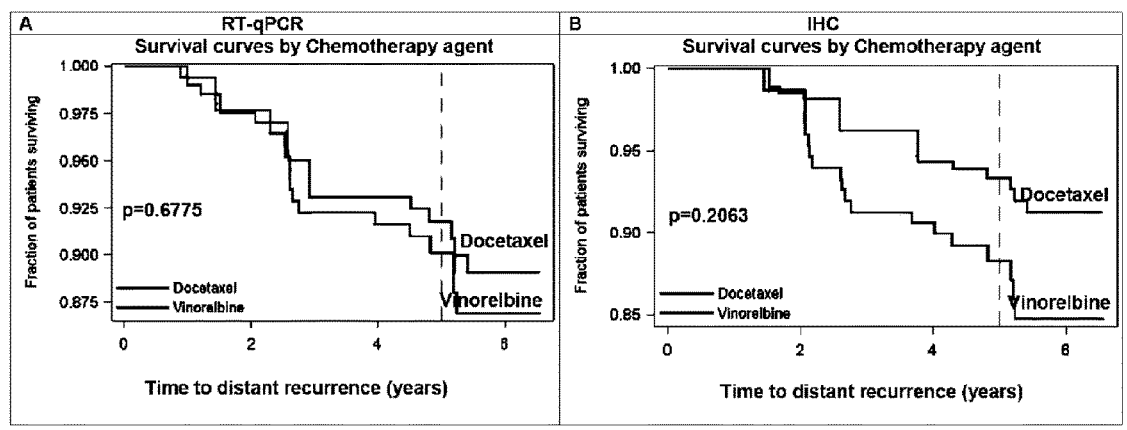

FIG. 17 depicts a Kaplan Meier analysis of distant metastasis free survival of luminal A tumor patients. A: en defined by RT-qPCR, luminal A patients do not differ in distant metastasis free survival upon treatment with docetaxel or vinorelbine (92% vs. 90%, HR 0.826; CI 0.336-2.033) B: IHC-subtyped patients treated with docetaxel as compared to vinorelbine show a weak, yet non-significant trend towards longer distant metastasis free survival (93% vs. 88%, HR 0.553; CI 0.221-1.386).

Figure 18:
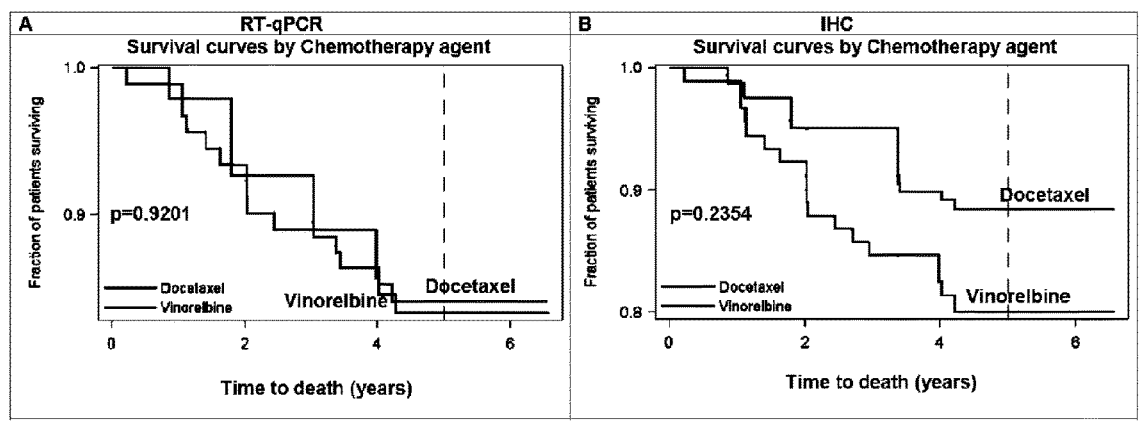

FIG. 18 depicts a Kaplan Meier analysis of overall survival of TNBC tumor patients. A: When defined by RT-qPCR, patients bearing TNBC exhibit no difference in overall survival upon treatment with docetaxel or vinorelbine (84% vs. 83%, HR 0.949; CI 0.338-2.665). B: When defined by IHC, TNBC patients show a weak, yet non-significant trend towards longer overall survival (88% vs. 80%, HR 0.552; CI 0.207-1.472).

Figure 19:
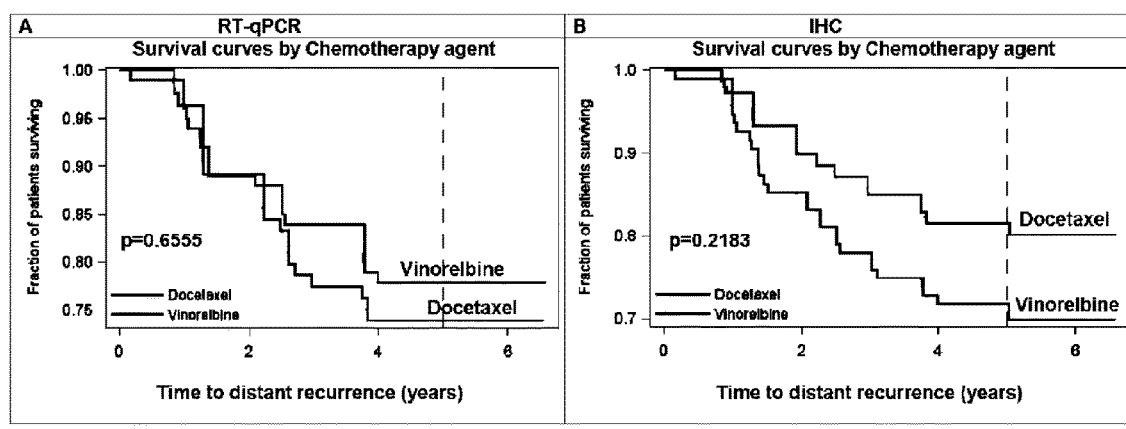

FIG. 19 depicts a Kaplan Meier analysis of distant metastasis free survival of TNBC tumor patients. A: Differently treated RT-qPCR-defined TNBC patients do not significantly differ in distant metastasis free survival (74% vs. 78%, HR 1.211; CI 0.523-2.802). B: IHC-defined TNBC patients show a weak, yet non-significant trend towards longer distant metastasis free survival (82% vs. 72%, HR 0.615; CI 0.284-1,333) when treated with docetaxel as compared to vinorelbine.

FIG. 20A shows a scatterplot of continuous Ki67 estimations by IHC (as depicted by % positive cells on the y-axis) and RT-qPCR (as depicted by 40-$\Delta\Delta$CT on the x-axis). Lines illustrate the predefined cut-off values of the statistical analysis plan (horizontal: IHC 20%; vertical: RT-qPCR 34.8 40-$\Delta\Delta$CT). B summarizes concordances and discordances between RT-qPCR and IHC based categorization (positive [pos] vs. negative [neg]). C shows Kappa statistics revealing a highly significant correlation ($p<0.0001$), but moderate concordance between methods. D shows the positive and negative percent agreement (PPA and NPA, respectively) when testing Ki67 by RT-qPCR vs. IHC.

Figure 21:
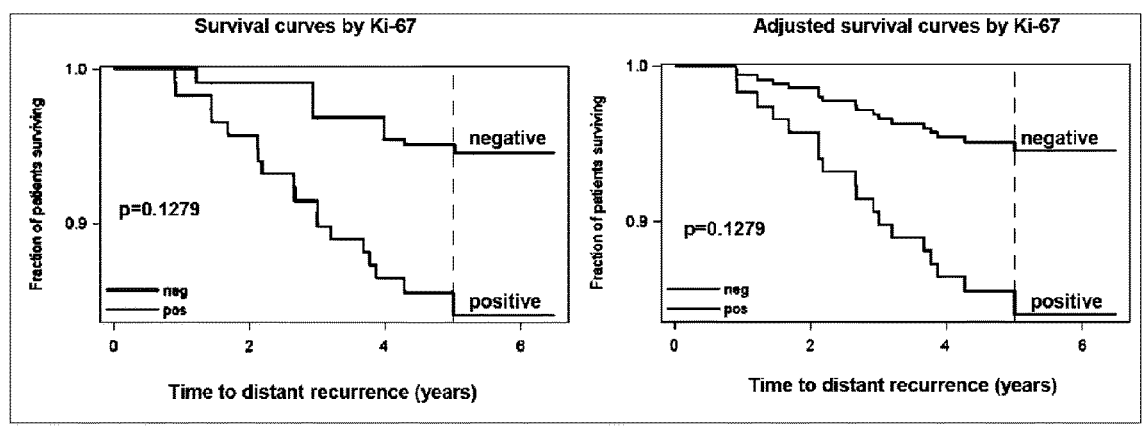

FIG. 21 depicts a Kaplan Meier analysis of distant metastasis free survival of patients with estrogen receptor positive tumors and discordant Ki67 results between RT-qPCR and IHC.

Other objects, advantages and features of the present invention will become apparent from the following detailed description, in particular when considered in conjunction with the accompanying figures.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In one aspect, the invention relates to an in vitro method of identifying a molecular subtype of a tumor in a cancer patient, said method comprising the steps:
(a) determining the expression level of RNA transcript of human epidermal growth factor receptor 2 (HER2) in a sample of the tumor;
(b) determining the expression level of RNA transcript of estrogen receptor (ESR1) in a sample of the tumor;
(c) determining the expression level of RNA transcript of progesterone receptor (PGR) in a sample of the tumor, and
(d) determining the expression level of RNA transcript of proliferation antigen Ki-67 (Ki67) in a sample of the tumor; and/or
(e) determining the expression level of RNA transcript of RacGTPase-activating protein 1 (RACGAP1) in a sample of the tumor.

In one embodiment, said method does not comprise the determination of the expression level, in particular the expression level of RNA transcript, of one or more additional non-reference genes. In other words, no expression level, in particular no expression level of RNA transcript, of a gene other than HER2, ESR1, PGR and Ki67 and/or RACGAP1 and one or more reference genes is determined.

In one embodiment, said method does not comprise any other diagnostic steps, such as histological grading or determining the lymph nodal status.

The term "tumor", as used herein, refers to all neoplastic cell growth and proliferation whether malignant or benign, and all pre-cancerous and cancerous cells and tissues. In one embodiment of the present invention, the tumor is a solid tumor. In one embodiment, the tumor is a breast tumor or is derived from a breast tumor (e.g. by metastasis).

As used herein, "cancer" includes a disease characterized by aberrantly regulated cellular growth, proliferation, differentiation, adhesion, and/or migration. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases. In one embodiment, the cancer is breast cancer.

The term "breast cancer" relates to a type of cancer originating from breast tissue, most commonly from the inner lining of milk ducts or the lobules that supply the ducts with milk. Cancers originating from ducts are known as ductal carcinomas, while those originating from lobules are known as lobular carcinomas. Occasionally, breast cancer presents as metastatic disease. Common sites of metastasis include bone, liver, lung and brain. Breast cancer occurs in humans and other mammals. While the overwhelming majority of human cases occur in women, male breast cancer can also occur. Treatment of breast cancer may include surgery, medications (hormonal therapy and chemotherapy), radiation and/or immunotherapy/targeted therapy.

The term "patient", as used herein, refers to any organism such as vertebrate, particularly any mammal, including both a human and another mammal, e.g., an animal such as a rodent, a rabbit, or a monkey. The rodent may be a mouse, rat, hamster, guinea pig, or chinchilla. Preferably, the patient is a human.

According to the present invention, the term "RNA transcript" includes and preferably relates to "mRNA" which means "messenger RNA" and relates to a "transcript" which encodes a peptide or protein. mRNA typically comprises a 5' non translated region (5'-UTR), a protein or peptide coding region and a 3' non translated region (3'-UTR). mRNA has a limited halftime in cells and in vitro.

The gene HER2 (also referred to as ERBB2; location: 17q12, annotation: chromosome: 17; NC_000017.10) encodes a member of the epidermal growth factor (EGF) receptor family of receptor tyrosine kinases. Amplification and/or overexpression of this gene have been reported in numerous cancers, including breast and ovarian tumors. In the NCBI database, two mRNA variants for HER2 are listed which code for two protein versions. Protein and mRNA sequences can be found under the accession numbers 001005862.1 (receptor tyrosine-protein kinase erbB-2 isoform b) and NM_004448.2 (receptor tyrosine-protein kinase erbB-2 isoform a precursor). HER2 gene amplification occurs in approx. 10-20% of primary breast carcinomas.

The gene ESR1 (location: 6q25, annotation: chromosome 6, NC_000006.11) encodes an estrogen receptor (ER), a ligand-activated transcription factor composed of several domains important for hormone binding, DNA binding, and activation of transcription. Estrogen receptors are known to be involved in pathological processes including breast cancer, endometrial cancer, and osteoporosis. Four ESR1 mRNA variants are known, wherein the transcript variants differ in the 5' UTR and/or use different promoters, but each variant codes for the same protein. 70-80% of all breast cancers are ER positive.

The gene PGR (also referred to as PR; location: 11q22-q23, annotation: chromosome: 11; NC_000011.9) encodes the progesterone receptor. Steroid hormones such as progesterone and their receptors are involved in the regulation of eukaryotic gene expression and affect cellular proliferation and differentiation in target tissues. This gene uses two distinct promoters and translation start sites in the first exon to produce two mRNA isoforms, A and B. The two isoforms are identical except for the additional 165 amino acids found in the N-terminus of isoform B. 40% of breast tumors are positive for PGR.

The gene Ki-67 (Ki67; location: 10q26.2, annotation: chromosome: 10; NC_000010.10) encodes a nuclear protein that is associated with and may be necessary for cellular proliferation. Two mRNA variants have been described. A related pseudogene exists on chromosome 10. Approximately 25% of breast tumors are positive for Ki67.

The gene RACGAP1 (location: 12q13.12, annotation: chromosome: 12; NC_000012.11) encodes for RacGTPase-activating protein 1. Three splice variants have been described, all encoding for the same protein. RACGAP1 is a component of the central spindlin complex and plays key roles in controlling growth-related processes and differentiation.

The term "expression level", as used herein, refers to the expression of a particular gene (i.e. HER2, ESR1, PGR, Ki67 or RACGAP1) so as to produce transcript and/or protein. According to the present invention, the expression level is determined on the RNA transcript level, in particular mRNA level (transcriptional level), for example, by measuring the transcribed mRNA (e.g., via northern blot), by reverse transcription (RT) quantitative PCR or by directly staining the mRNA (e.g., via in situ hybridization).

In one embodiment, the term "sample of the tumor" refers to a tumor tissue sample isolated from the cancer patient (e.g., a biopsy or resection tissue of the tumor). In a preferred embodiment, the tumor tissue sample is a cryo-section of a tumor tissue sample or is a chemically fixed tumor tissue sample. In a more preferred embodiment, the tumor tissue sample is a formalin-fixed and paraffin-embedded (FFPE) tumor tissue sample. In one embodiment, the sample of the tumor is (total) RNA extracted from the tumor tissue sample. In a particularly preferred embodiment, the sample of the tumor is (total) RNA extracted from a FFPE tumor tissue sample. Those skilled in the art are able to perform RNA extraction procedures. For example, total RNA from a 5 to 10 μm curl of FFPE tumor tissue can be extracted using the High Pure RNA Paraffin Kit (Roche, Basel, Switzerland) or, preferably, the XTRAKT RNA Extraction Kit XL (Stratifyer Molecular Pathology, Cologne, Germany). It is also possible to store the sample material to be used/tested in a freezer and to c out the method of the present invention at an appropriate point in time after thawing the respective sample material. The sample may be obtained from the cancer patient prior to initiation of a therapeutic treatment, during the therapeutic treatment, and/or after the therapeutic treatment, i.e. prior to, during or following the administration of cancer therapy.

The term "molecular subtype of a tumor", as used herein, refers to subtypes of a tumor that are characterized by distinct molecular profiles, e.g., gene expression profiles. In one embodiment, the molecular subtype is selected from the group comprising HER2-positive, triple-negative (also referred to as "basal-like"), luminal A and luminal B. The term "basal-like" refers to the fact that such tumors have some similarity in gene expression to that of basal epithelial cells. The term "luminal" derives from the similarity in gene expression between the tumors and the luminal epithelium.

The molecular subtypes differ markedly in clinical outcome and response to therapy. In one embodiment, the molecular subtype luminal A, as defined herein, is associated with a probability of distant recurrence-free survival 5 years after treatment which is at least 11%, preferably at least 13% higher than the probability of distant recurrence-free survival 5 years after treatment associated with molecular subtype luminal B and/or with a probability of survival 5 years after treatment which is at least 7%, preferably at least 9% higher than the probability of survival 5 years after treatment associated with molecular subtype luminal B.

The term "(therapeutic) treatment", in particular in connection with the treatment of cancer as used herein, relates to any treatment which improves the health status and/or prolongs (increases) the lifespan of a patient. Said treatment may eliminate cancer, reduce the size or the number of tumors in a patient, arrest or slow the development of cancer in a patient, inhibit or slow the development of new cancer in a patient, decrease the frequency or severity of symptoms in a patient, and/or decrease recurrences in a patient who currently has or who previously has had cancer. In one embodiment, the terms "treatment" and "therapeutic treatment" are meant to refer to one or more of surgical removal of the primary tumor, chemotherapy, hormonal therapy, radiation therapy and immunotherapy/targeted therapy.

Adjuvant therapy is a treatment that is given in addition to the primary, main or initial treatment. The surgeries and complex treatment regimens used in cancer therapy have led the term to be used mainly to describe adjuvant cancer treatments. An example of adjuvant therapy is the additional treatment (e.g., chemotherapy) usually given after surgery (post-surgically), where all detectable disease has been removed, but where there remains a statistical risk of relapse due to occult disease. Neoadjuvant therapy is treatment given before the primary, main or initial treatment (e.g., pre-surgical chemotherapy).

In accordance with the present invention, the step of "determining the expression level of RNA transcript" may comprise (i) measuring the expression level of RNA transcript and (ii) analyzing the measured expression level of RNA transcript (e.g., by comparison to a reference expression level, such as a defined expression threshold), wherein the order of measuring the expression level of RNA transcript of HER2, ESR1, PGR and Ki67 and/or RACGAP1 is independent of the order of analyzing the measured expression level of RNA transcript of HER2, ESR1, PGR and Ki67 and/or RACGAP1.

In one embodiment, determining the expression level of RNA transcript of HER2, ESR1, PGR and Ki67 and/or RACGAP1 comprises determining whether the expression level of RNA transcript of HER2, ESR1, PGR and Ki67 and/or RACGAP1 is lower or higher than a defined expression threshold of RNA transcript of HER2, ESR1, PGR and Ki67 and/or RACGAP1. In cases where the expression level is equal to the defined expression threshold, the expression level is considered to belong to the group of expression levels that are higher than the defined expression threshold. Thus, the wording "higher than a defined expression threshold", as used herein, includes expression levels that are higher than or equal to the defined expression threshold. Expression levels that are "higher than a defined expression threshold" may also be referred to as "expression-positive", whereas expression levels that are "lower than a defined expression threshold" may also be referred to as "expression-negative"

The term "defined expression threshold of RNA transcript", as used herein, may refer to the mean cut-off value (in short: cut-off) calculated from a number of samples, said number of samples being obtained from a number of subjects, in particular, subjects having cancer. To obtain the threshold, the number of subjects may include subjects having tumors of different molecular subtypes, e.g., subjects having HER2-positive tumors and/or subjects having triple-negative tumors and/or subjects having luminal A tumors and/or subjects having luminal B tumors. The threshold may represent an amount or concentration of the RNA transcript. In one embodiment, the threshold is given as CT (cycle threshold) value (see below). In one embodiment, the (relative) expression level and expression threshold are expressed as 40-ΔCT or 40-ΔΔCT values (see below).

The term "subject", as used herein, relates to any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the subject is a human. In one embodiment, a subject is a subject with or suspected of having a disease, in particular cancer, also designated "patient" herein. For the determination of the mean cut-off value, at least two subjects, preferably at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, or at least 2000 subjects, are tested.

As various clinical studies have already been conducted with the gene markers used in accordance with the present invention, a concordance study in a training-testing setting will be sufficient for the definition and validation of a clinical cut-off/threshold for dichotomization of quantitative results in "expression-positive" or "expression-negative". Thus, in one embodiment, the cut-off/threshold is defined based on one or more previous clinical studies. Moreover, additional clinical studies may be conducted for the establishment and validation of the cut-off/threshold. The cut-off/threshold may be determined/defined by techniques known in the art.

In one embodiment, the cut-off/threshold is determined/defined on the basis of clinico-pathologic parameters, such as IHC-ISH, and/or the data for overall survival (OS), disease-free survival (DFS), and distant metastasis free survival (DMFS), and disease-specific survival (DSS) in training cohorts (e.g., HE10-97, Pentheroudakis et al. (2009), Breast Cancer Res Treat, 116: 131-143) by portioning tests (e.g., SAS Software JMP® 9.0.0) and validated in independent clinical trial cohorts, e.g., FFPE tissue samples of the FinHER study (Joensuu et al. (2006), N Engl J Med, 354: 809-820).

In one embodiment, the 40-$\Delta$CT value is calculated as follows: 40–[CT of the respective biomarker (i.e. HER2, ESR1, PGR and Ki67 and/or RACGAP1) of a patient sample–CT of a reference gene (e.g., CALM2) of a patient sample] (=calculation method 1). If more than one reference gene is used, the 40-$\Delta$CT value is calculated as follws: 40–(CT of the respective biomarker of a patient sample–mean CT of selected reference genes of a patient sample) (=calculation method 2). Alternatively, a 40-$\Delta\Delta$CT value can be used, wherein the 40-$\Delta\Delta$CT can be calculated as follows: $\Delta\Delta$CT=40–[(CT biomarker of a patient sample–CT biomarker of a reference sample)–(CT reference gene of patient sample–CT reference gene of a reference sample)] (=calculation method 3); e.g., 40-$\Delta\Delta$CT=40–[(CT Ki67 patient sample–CT Ki67 reference sample)–(CT CALM2 of a patient sample–CT CALM2 of a reference sample)]. In one embodiment, CALM2 is used as reference gene.

In an exemplary embodiment, the mean cut-off value is given as a 40-$\Delta$CT value according to calculation method 2, wherein the mean cut-off value for HER2 is a 40-$\Delta$CT value of 38, the mean cut-off value for ESR1 is a 40-$\Delta$CT value of 34, the mean cut-off value for PGR is a 40-$\Delta$CT value of 30.2, the mean cut-off value for Ki67 is a 40-$\Delta$CT value of 31.7, and the mean cut-off value for RACGAP1 is a 40-$\Delta$CT value of 34.2.

In another embodiment, the relative expression level of the biomarkers is given as a 40-$\Delta\Delta$CT value, which is calculated as follows: 40–[(CT biomarker of a patient sample–CT reference gene of the patient sample)–(CT biomarker of a control sample–CT reference gene of the control sample)] (=calculation method 4); e.g., 40-$\Delta\Delta$CT=40–[(CT Ki67 patient sample–CT Mean CombRef patient sample)–(CT Ki67 control sample–CT Mean CombRef control sample)]. In one embodiment, the CT is the median CT. The CT of the reference gene can be the CT of a single reference gene or the mean CT of two or more reference genes (referred to as Mean CombRef). Preferably, the same control sample (also referred to as calibrator) is used in all analyses and leads to the same RT-qPCR or qPCR results. In one embodiment, the control sample is a cell line RNA, an in vitro transcribed artificial RNA or an equimolar mixture of DNA oligonucleotides, representing the biomarker mRNA or cDNA or the biomarker amplicon or a part of the biomarker amplicon with a constant ratio. In one embodiment, CALM2 and B2M are used as reference genes and a positive control (e.g., in vitro transcribed artificial RNA) is used as control sample (calibrator).

In an exemplary embodiment, the mean cut-off value is given as a 40-$\Delta\Delta$CT value according to calculation method 4, wherein the mean cut-off value for HER2 is a 40-$\Delta\Delta$CT value of 40.90, the mean cut-off value for ESR1 is a 40-$\Delta\Delta$CT value of 38.20, the mean cut-off value for PGR is a 40-$\Delta\Delta$CT value of 34.90 and the mean cut-off value for Ki67 is a 40-$\Delta\Delta$CT value of 34.80 on a Versant kPCR Instrument AD module (Siemens).

In another exemplary embodiment, the mean cut-off value is given as a 40-$\Delta\Delta$CT value according to calculation method 4, wherein the mean cut-off value for HER2 is a 40-$\Delta\Delta$CT value of 41.1, the cut-off value for ESR1 is a 40-$\Delta\Delta$CT value of 38.00, the cut-off value for PGR is a 40-$\Delta$CT value of 35.50 and the cut-off value for Ki67 is a 40-$\Delta\Delta$CT value of 35.50 on a LightCycler® 480 instrument II (Roche).

In one embodiment, steps (a), (b), (c) and (d) and/or (e) are performed in random order. In one embodiment, step (a) is performed before steps (b), (c) and (d) and/or (e). In one embodiment, step (d) and/or step (e) are performed after steps (a), (b) and (c). In one embodiment, step (a) is performed before step (b), step (b) is performed before step (c), and step (c) is performed before step (d) and/or step (e).

In one embodiment, an expression level of RNA transcript of HER2 which is higher than a defined expression threshold of RNA transcript of HER2 identifies the molecular subtype of the tumor as HER2-positive.

In one embodiment,
an expression level of RNA transcript of HER2 which is lower than a defined expression threshold of RNA transcript of HER2;
an expression level of RNA transcript of ESR1 which is lower than a defined expression threshold of RNA transcript of ESR1;
an expression level of RNA transcript of PGR which is lower than a defined expression threshold of A transcript of PGR; and
an expression level of RNA transcript of Ki67 which is lower or higher than a defined expression threshold of RNA transcript of Ki67
identify the molecular subtype of the tumor as triple-negative.

In one embodiment, the molecular subtype is luminal A or luminal B.

In one embodiment,
an expression level of RNA transcript of HER2 which is lower than a defined expression threshold of RNA transcript of HER2;
an expression level of RNA transcript of ESR1 which is higher than a defined expression threshold of RNA transcript of ESR1;

an expression level of RNA transcript of PGR which is higher than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is higher than a defined expression threshold of RNA transcript of PGR; and an expression level of RNA transcript of Ki67 which is lower than a defined expression threshold of RNA transcript of Ki67 identify the molecular subtype of the tumor as luminal A.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is lower than a defined expression threshold of RNA transcript of PGR; and an expression level of RNA transcript of Ki67 which is lower or higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is lower than a defined expression threshold of RNA transcript of ESR1;

an expression level of RNA transcript of PGR which is higher than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, an expression level of RNA transcript of HER2 which is lower than a defined expression threshold of RNA transcript of HER2;

an expression level of RNA transcript of ESR1 which is lower than a defined expression threshold of RNA transcript of ESR1;

an expression level of RNA transcript of PGR which is higher than a defined expression threshold of RNA transcript of PGR; and an expression level of RNA transcript of Ki67 which is lower than a defined expression threshold of RNA transcript of Ki67 identify the molecular subtype of the tumor as luminal A.

In one embodiment, an expression level of RNA transcript of HER2 which is lower than a defined expression threshold of RNA transcript of HER2;

an expression level of RNA transcript of ESR1 which is higher than a defined expression threshold of RNA transcript of ESR1;

an expression level of RNA transcript of PGR which is lower than a defined expression threshold of RNA transcript of PGR; and an expression level of RNA transcript of Ki67 which is higher than a defined expression threshold of RNA transcript of Ki67 identify the molecular subtype of the tumor as luminal B.

In one embodiment, the method comprises step (d), and an expression level of RNA transcript of ESR1 which is higher than a defined expression threshold of RNA transcript of ESR1 and an expression level of RNA transcript of Ki67 which is higher than a defined expression threshold of RNA transcript of Ki67 indicates an increased risk of poor clinical outcome for the cancer patient, in particular an increased risk of distant metastasis.

In one embodiment, the method comprises step (e), and an expression level of RNA transcript of CGAP1 which is higher than a defined expression threshold of RNA transcript of RACGAP1 indicates an increased risk of poor clinical outcome for the cancer patient (as compared to the risk of a cancer patient with a tumor having an expression level of RNA transcript of RACGAP1 which is lower than the defined expression threshold of RNA transcript of RAC-GAP1).

The determination of the expression level of RNA transcript of both Ki67 and RACGAP1 provides more precise information regarding the clinical outcome of a cancer patient, wherein, generally, an increased expression level of RNA transcript of either Ki67 or RAC indicates an increased risk of poor clinical outcome for the cancer patient (as compared to the risk of a cancer patient with a tumor having an expression level of RNA transcript of Ki67 or CGAP1 which is lower than the defined expression threshold of RNA transcript of Ki67 or CGAP1).

In one embodiment, the method comprises steps (d) and (e), and an expression level of RNA transcript of Ki67 which is lower than a defined expression threshold of RNA transcript of Ki67 and an expression level of RNA transcript of RACGAP1 which is higher than a defined expression threshold of RNA transcript of RACGAP1 indicates an increased risk of poor clinical outcome for the cancer patient.

In one embodiment, the method comprises steps (d) and (e), and an expression level of RNA transcript of Ki67 which is higher than a defined expression threshold of RNA transcript of Ki67 and an expression level of RNA transcript of RACGAP1 which is higher than a defined expression threshold of RNA transcript of RACGAP1 indicates a further increased risk of poor clinical outcome for the cancer patient (as compared to the increased risk of a cancer patient with a tumor having an expression level of RNA transcript of Ki67 which is lower than a defined expression threshold of RNA transcript of Ki67 and an expression level of RNA transcript of RACGAP1 which is higher than the defined expression threshold of RNA transcript of RACGAP1, wherein, preferably, the further increase refers to an increase by at least 5%, more preferably by at least 10%).

The term "clinical outcome" is defined as the clinical result of a disease, in particular following a treatment, e.g., reduction or amelioration of symptoms. In one embodiment, poor clinical outcome comprises a relative reduction in or more of survival, recurrence-free survival and distant recurrence-free survival. The term "recurrence" with respect to cancer includes re-occurrence of tumor cells at the same site and organ of the origin disease, metastasis that can appear even many years after the initial diagnosis and therapy of cancer, or to local events such as infiltration of tumor cells into regional lymph nodes. "Distant recurrence" refers to a scenario, where the cancer cells have spread (metastasized) to a distant part (i.e., another organ) of the body beyond the regional lymph nodes. Recurrence-free survival is generally defined as the time from randomization to the first of recurrence, relapse, second cancer, or death.

The term "metastasis" is meant to refer to the spread of cancer cells from their original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary or because tumor cells or components may remain and develop metastatic potential.

In one embodiment, an "increased risk of poor clinical outcome" refers to a probability of survival 5 years after treatment which is at least 20% lower, preferably at least 25% lower than the probability of survival 5 years after treatment of a cancer patient with a tumor having
- an expression level of RNA transcript of Ki67 which is lower than a defined expression threshold of RNA transcript of Ki67 and
- an expression level of RNA transcript of RACGAP1 which is lower than a defined expression threshold of RNA transcript of RACGAP1.

In one embodiment, a "further increased risk of poor clinical outcome" refers to a probability of survival 5 years after treatment which is at least 30% lower, preferably at least 35% lower than the probability of survival 5 years after treatment of a cancer patient with a tumor having
- an expression level of RNA transcript of Ki67 which is lower than a defined expression threshold of RNA transcript of Ki67 and
- an expression level of RNA transcript of RACGAP1 which is lower than a defined expression threshold of RNA transcript of RACGAP1.

In one embodiment, the expression level of RNA transcript is determined by reverse transcription (RT) quantitative PCR (RT-qPCR). As RNA cannot be directly amplified in PCR, it must be reverse transcribed into cDNA using the enzyme reverse transcriptase. For this purpose, a one-step RT-qPCR can be utilized, which combines the reactions of reverse transcription with DNA amplification by PCR in the same reaction. In one-step RT-qPCR, the RNA template is mixed in a reaction mix containing reverse transcriptase, DNA polymerase, primers and probes, dNTPs, salts and detergents. In a first PCR step, the target RNA is reverse transcribed by reverse transcriptase using the target specific reverse primers. Afterwards, the cDNA is amplified using the primers/probes and DNA polymerase.

In one embodiment, the quantitative PCR is fluorescence-based quantitative real-time PCR. The fluorescence-based quantitative real-time PCR comprises the use of a fluorescently labeled probe. Preferably, the fluorescently labeled probe consists of an oligonucleotide labeled with both a fluorescent reporter dye and a quencher dye (=dual-label probe). Suitable fluorescent reporter and quencher dyes/moieties are known to a person skilled in the art and include, but are not limited to the reporter dyes/moieties 6-F™, JOE™, Cy5®, Cy3® and the quencher dyes/moieties dabcyl, TAMRA™, BHQ™-1, -2 or -3. Amplification of the probe-specific product causes cleavage of the probe (=amplification-mediated probe displacement), thereby generating an increase in reporter fluorescence. The increase of fluorescence in the reaction is directly proportional to the increase of target amplificates. By using the LightCycler 480 II system (Roche) or the Versant kPCR system (Siemens) or the Mx3005P system (Agilent Technologies) or equivalent real-time instruments for detection of fluorescence originating from the probe, one can measure the increase in fluorescence in real-time. Analysis output is a CT value of each target. The CT (cycle threshold) value is determined by the number of PCR amplification cycles, after which the fluorescence signal of the probe exceeds a certain background signal, wherein the CT value is a measure for the amount of target molecules in the sample before the PCR amplification. Preferably, CT-values are further analyzed with appropriate software (e.g., Microsoft Excel™) or statistical software packages (e.g., SAS JMP® 9.0.0, GraphPad Prism4, Genedata Expressionist™). The CT value can either be converted to an absolute target molecule amount (e.g., ng/µl or molecules/µl) based on the CT results of a standard curve with known target concentrations. Alternatively, the target amount can be reported as x-fold decreased or increased amount based on a reference (=$\Delta$CT). Low $\Delta$CT values (small difference) indicate higher amounts of target relative to the reference compared to high $\Delta$CT (big difference). It is suitable to re-calculate the $\Delta$CT by subtracting it from a fixed value (such as the number of PCR cycles, e.g. 40). The result is a value with direct correlation to target amount (high value=high amount) and expressed as 40-$\Delta$CT values, wherein one integer refers to a doubling of the target amount (e.g., a value of 34 indicates an amount which is twice as much as that with a value of 33). Depending on the desired reproducibility and precision of the system, it is possible to panel multiple reference assays or to re-calculate/normalize the $\Delta$CT of the sample with the $\Delta$CT of a calibrator (1 point calibration; Pfaffl (2001), Nucleic Acid Res., 29(9):e45). By using different fluorophores for specific probes it is also possible to multiplex different target assays in the same reaction. During PCR, each target in the multiplex is amplified in parallel, but separately detected utilizing the different fluorescent emission.

Preferably, primers for use in accordance with the present invention have a length of 15 to 30 nucleotides, in particular deoxyribonucleotides. In one embodiment, the primers are designed so as to (1) be specific for the target mRNA-sequence (i.e. HER2, ESR1, PGR and Ki67 and/or RACGAP1), (2) provide an amplicon size of less than 120 by (preferably less than 100 bp), (3) detect all known protein-encoding splicing variants, (4) not include known polymorphisms (e.g., single nucleotide polymorphisms, SNPs), (5) be mRNA-specific (consideration of exons/introns; preferably no amplification of DNA), (6) have no tendency to dimerize and/or (7) have a melting temperature $T_m$ in the range of from 58° C. to 62° C. (preferably, $T_m$ is approximately 60° C.).

As used herein, the term "nucleotide" includes native (naturally occurring) nucleotides, which include a nitrogenous base selected from the group consisting of adenine (A), thymidine (T), cytosine (C), guanine (G) and uracil (U), a sugar selected from the group of ribose, arabinose, xylose, and pyranose, and deoxyribose (the combination of the base and sugar generally referred to as a "nucleoside"), and one to three phosphate groups, and which can form phosphodiester internucleosidyl linkages. Further, as used herein, "nucleotide" refers to nucleotide analogues. As used herein, "nucleotide analogue" shall mean an analogue of A, G, C, T or U (that is, an analogue of a nucleotide comprising the base A, G, C, T or U) which is recognized by DNA or RNA polymerase (whichever is applicable) and incorporated into a strand of DNA or RNA (whichever is appropriate). Examples of such nucleotide analogues include, without limitation, 5-propynyl pyrimidines (i.e., 5-propynyl-dTTP and 5-propynyl-dCTP), 7-deaza purines (i.e., 7-deaza-dATP and 7-deaza-dGTP), aminoallyl-dNTPs, biotin-AA-dNTPs, 2-amino-dATP, 5-methyl-dCTP, 5-iodo-dUTP, 5-bromo-dUTP, 5-fluoro-dUTP, N4-methyl-dCTP, 2-thio-dTTP, 4-thio-dTTP and alpha-thio-dNTPs. Also included are labelled analogues, e.g. fluorescent analogues such as DEAC-propylenediamine (PDA)–ΔTP, analogues based on morpholino nucleoside analogues as well as locked nucleic acid (LNA) analogues.

The wording "specific for the target mRNA-sequence", as used in connection with primers for use in accordance with the present invention, is meant to refer to the ability of the primer to hybridize (i.e. anneal) to the cDNA of the target mRNA-sequence under appropriate conditions of temperature and solution ionic strength, in particular PCR conditions. The conditions of temperature and solution ionic strength determine the stringency of hybridization. Hybridization requires that the two nucleic acids (i.e. primer and cDNA) contain complementary sequences, although depending on the stringency of the hybridization, mismatches between bases are possible. In one embodiment, "appropriate conditions of temperature and solution ionic strength" refer to a temperature in the range of from 58° C. to 62° C. (preferably a temperature of approximately 60° C.) and a solution ionic strength commonly used in PCR reaction mixtures. In one embodiment, the sequence of the primer is 80%, preferably 85%, more preferably 90%, even more preferably 95%, 96%, 97%, 98%, 99% or 100% complementary to the corresponding sequence of the cDNA of the target mRNA-sequence, as determined by sequence comparison algorithms known in the art.

In one embodiment, the primer hybridzes to the cDNA of the target mRNA-sequence under stringent or moderately stringent hybridization conditions. "Stingent hybridization conditions", as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). "Moderately stringent hybridization conditions", as defined herein, involve including washing in 3×SSC at 42° C., or the art-recognized equivalent thereof. The parameters of salt concentration and temperature can be varied to achieve the optimal level of identity between the primer and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley and Sons, N.Y.).

In one embodiment, the method of the present invention comprises the use of ESR1-specific primers having a length of 15 to 30 nucleotides and comprising at least 10 contiguous nucleotides of the sequences of SEQ ID NOs: 1 and 2, and/or HER2-specific primers having a length of 15 to 30 nucleotides and comprising at least 10 contiguous nucleotides of the sequences of SEQ ID NOs: 4 and 5, and/or Ki67-specific primers having a length of 15 to 30 nucleotides and comprising at least 10 contiguous nucleotides of the sequences of SEQ ID NOs: 7 and 8, and/or PGR-specific primers having a length of 15 to 30 nucleotides and comprising at least 10 contiguous nucleotides of the sequences of SEQ ID NOs: 10 and 11, and/or RACGAP1-specific primers having a length of 15 to 30 nucleotides and comprising at least 10 contiguous nucleotides of the sequences of SEQ ID NOs: 13 and 14. In one embodiment, the specific primers comprise at least 15 contiguous nucleotides of the sequences indicated above.

In one embodiment, the method comprises the use of ESR1-specific primers having the sequences of SEQ ID NOs: 1 and 2, and/or HER2-specific primers having the sequences of SEQ NOs: 4 and 5, and/or Ki67-specific primers having the sequences of SEQ ID NOs: 7 and 8, and/or PGR-specific primers having the sequences of SEQ ID NOs: 10 and 11, and/or RACGAP1-specific primers having the sequences of SEQ ID NOs: 13 and 14.

Preferably, probes for use in accordance with the present invention have a length of 20 to 35 nucleotides, in particular deoxyribonucleotides. In one embodiment, the probes are designed so as to (1) be specific for the target mRNA-sequence (i.e. HER2, ESR1, PGR and Ki67 and/or RACGAP1), (2) not include known polymorphisms (e.g., single nucleotide polymorphisms, SNPs) and/or (3) have a melting temperature $T_m$, which is approximately 5° C. to 8° C. higher than the melting temperature $T_m$ of the corresponding primer(s).

The wording "specific for the target mRNA-sequence", as used in connection with probes for use in accordance with the present invention, is meant to refer to the ability of the probe to hybridize (i.e. anneal) to the (amplified) cDNA of the target mRNA-sequence under appropriate conditions of temperature and solution ionic strength, in particular PCR conditions. The conditions of temperature and solution ionic strength determine the stringency of hybridization. Hybridization requires that the two nucleic acids (i.e. probe and cDNA) contain complementary sequences, although depending on the stringency of the hybridization, mismatches between bases are possible. In one embodiment, "appropriate conditions of temperature and solution ionic strength" refer to a temperature in the range of from 63° C. to 70° C. and a solution ionic strength commonly used in PCR reaction mixtures. In one embodiment, the sequence of the probe is 80%, preferably 85%, more preferably 90%, even more preferably 95%, 96%, 97%, 98%, 99% or 100% complementary to the corresponding sequence of the (amplified) cDNA of the target mRNA-sequence, as determined by sequence comparison algorithms known in the art.

In one embodiment, the probe hybridizes to the (amplified) cDNA of the target mRNA-sequence under stringent or moderately stringent hybridization conditions as defined above.

In one embodiment, the method comprises the use of an ESR1-specific probe having a length of 20 to 35 nucleotides and comprising at least 15 contiguous nucleotides of the sequence of SEQ ID NO: 3, and/or a HER2-specific probe having a length of 20 to 35 nucleotides and comprising at least 15 contiguous nucleotides of the sequence of SEQ ID NO: 6, and/or a Ki67-specific probe having a length of 20 to 35 nucleotides and comprising at least 15 contiguous nucleotides of the sequence of SEQ ID NO: 9, and/or a PGR-specific probe having a length of 20 to 35 nucleotides and comprising at least 15 contiguous nucleotides of the sequence of SEQ ID NO: 12, and/or a RACGAP1-specific probe having a length of 20 to 35 nucleotides and comprising at least 15 contiguous nucleotides of the sequence of SEQ ID NO: 15. In one embodiment, the specific probes comprise at least 20 contiguous nucleotides of the sequences indicated above.

In one embodiment, the method comprises the use of an ESR1-specific probe having the sequence of SEQ ID NO: 3, and/or a HER2-specific probe having the sequence of SEQ ID NO: 6, and/or a Ki67-specific probe having the sequence of SEQ ID NO: 9, and/or a PGR-specific probe having the sequence of SEQ ID NO: 12, and/or a RACGAP1-specific probe having the sequence of SEQ ID NO: 15.

Preferably, the probes as defined above are dual-label probes comprising a fluorescence reporter moiety and a fluorescence quencher moiety.

In one embodiment, the expression level is normalized against the (mean) expression level of one or more reference genes in the sample of the tumor. The term "reference gene", as used herein, is meant to refer to a gene which has a relatively invariable level of expression on the RNA transcript/mRNA level in the system which is being examined, i.e. cancer. Such gene may be referred to as housekeeping gene. In one embodiment, the one or more reference genes are selected from the group comprising CALM2, B2M, RPL37A, GUSB, HPRT1 and GAPDH, preferably CALM2 and/or B2M.

As used herein, CALM2 refers to calmodulin-2, phosphorylase kinase, delta (RefSeq. (mRNA): NM_001743), B2M refers to beta-2 microglobulin (Ref.Seq. (mRNA): NM_004048), RPL37A refers to 60S ribosomal protein L37a (Ref.Seq. (mRNA): NM_000998), GUSB refers to beta-glucuronidase (Ref.Seq. (mRNA): NM_000181), HPRT1 refers to hypoxanthine-phosphoribosyl-transferase 1 (Ref.Seq. (mRNA): NM_000194) and GAPDH refers to glycerinaldehyde-3-phosphate-dehydrogenase (Ref.Seq. (mRNA): NM_002046).

In a further aspect, the invention relates to a method of stratifying a cancer patient for tumor treatment, said method comprising, as a first step, identifying a molecular subtype of a tumor in the cancer patient using the in vitro method as defined above and, as a second step, selecting a tumor treatment regimen based on the molecular subtype identified by the in vitro method.

"Stratifying a cancer patient for tumor treatment" in accordance with the present invention comprises the allocation of the cancer patient to a patient group having a particular molecular tumor subtype, which then allows the medical practitioner to select the most suitable tumor treatment regimen.

In one embodiment, said method of stratifying a cancer patient for tumor treatment does not comprise any other diagnostic steps, such as histological grading or determining the lymph nodal status, besides the step of identifying the molecular subtype of the tumor in the cancer patient using the in vitro method as defined above.

In one embodiment, the molecular subtype is selected from the group comprising HER2-positive, triple-negative, luminal A and luminal B.

In one embodiment,
the molecular subtype is HER2-positive, and the tumor treatment regimen comprises administration of anti-HER2 antibodies and chemotherapeutic agents;

the molecular subtype is triple-negative, and the tumor treatment regimen comprises administration of chemotherapeutic agents;

the molecular subtype is luminal A, and the tumor treatment regimen comprises endocrine therapy; or the molecular subtype is luminal B, and the tumor treatment regimen comprises endocrine therapy and, optionally, administration of chemotherapeutic agents.

Monoclonal anti-HER2 antibodies include trastuzumab (Herceptin®) and pertuzumab (Perjeta®), which may be administered alone or combination. Trastuzumab is effective only in cancers where HER2 is over-expressed. Other monoclonal antibodies, such as ertumaxomab (Rexomun®), are presently undergoing clinical trials. The anti-HER2 antibodies can further be modified to comprise a therapeutic moiety/agent, such as a cytotoxic agent, a drug (e.g., an immunosuppressant), a chemotherapeutic agent or a radionuclide, or a radioisotope. A cytotoxin or cytotoxic agent includes any agent that is detrimental to and, in particular, kills cells. Examples include mertansine (DM1), taxol, cytochalasin B, gramicidin D, ethidium bromide, emetine, mitomycin, etoposide, tenoposide, vincristine, vinblastine, colchicin, doxorubicin, daunorubicin, dihydroxy anthracin, dione, mitoxantrone, mithramycin, actinomycin D, amanitin, 1-dehydrotestosterone, glucocorticoids, procaine, tetracaine, lidocaine, propranolol, and puromycin and analogs or homologs thereof. Other suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepachlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A. Further therapeutic moieties include therapeutic moieties acting on mRNA and/or protein synthesis. Several inhibitors of transcription are known. For instance, actinomycin D, which is both a transcriptional inhibitor and a DNA damage agent, intercalates within the DNA and thus inhibits the initiation stage of transcription. Flavopiridol targets the elongation stage of transcription, α-Arnanitin binds directly to RNA polymerase II, which leads to the inhibition of both initiation and elongation stages. Anti-HER2 Antibodies also can be conjugated to a radioisotope, e.g., iodine-131, yttrium-90 or indium-111, to generate cytotoxic radiopharmaceuticals. An alternative to the administration of anti-HER2 antibodies is the administration of small compounds targeting HER2, such as lapatinib (Tykerb® or Tyverb®).

Chemotherapeutic agents according to the invention include cytostatic compounds and cytotoxic compounds. Traditional chemotherapeutic agents act by killing cells that divide rapidly, one of the main properties of most cancer cells. According to the invention, the term "chemotherapeutic agent" includes taxanes, platinum compounds, nucleoside analogs, camptothecin analogs, anthracyclines and anthracycline analogs, etoposide, bleomycin, vinorelbine, cyclophosphamide, antimetabolites, anti-mitotics, and alkylating agents, including the agents disclosed above in connection with antibody conjugates, and combinations thereof. According to the invention a reference to a chemotherapeutic agent is to include any prodrug such as ester, salt or derivative such as a conjugate of said agent. Examples are conjugates of said agent with a carrier substance, e.g., protein-bound paclitaxel such as albumin-bound paclitaxel. Preferably, salts of said agent are pharmaceutically acceptable. Chemotherapeutic agents are often given in combinations, usually for 3-6 months. One of the most common treatments is cyclophosphamide plus doxorubicin (adriamycin; belonging to the group of anthracyclines and anthracycline analogs), known as AC. Sometimes, a taxane drug, such as docetaxel, is added, and the regime is then known as CAT; taxane attacks the microtubules in cancer cells. Another common treatment, which produces equivalent results, is cyclophosphamide, methotrexate, which is an antimetabolite, and fluorouracil, which is a nucleoside analog (CMF). Another standard chemotherapeutic treatment comprises fluorouracil, epirubicin and cyclophosphamide (FEC), which may be supplemented with docetaxel or vinorelbine.

Endocrine therapy (anti-hormonal treatment) targets cancers that require estrogen to continue growing by administration of drugs that either block/down-regulate estrogen and/or progesterone receptors, e.g., tamoxifen (Nolvadex®) or fulvestrant (Faslodex®), or alternatively block the production of estrogen with an aromatase inhibitor, e.g., anastrozole (Arimidex®) or letrozole (Femara®). Aromatase inhibitors, however, are only suitable for post-menopausal patients. This is because the active aromatase in postmenopausal women is different from the prevalent form in premenopausal women, and therefore these agents are ineffective in inhibiting the predominant aromatase of premenopausal women.

In one embodiment, the molecular subtype is luminal B, and the tumor treatment regimen comprises administration of chemotherapeutic agents.

In one embodiment, the molecular subtype is luminal B, and the tumor treatment regimen comprises administration of a taxane, preferably docetaxel.

In one embodiment, the taxane is administered in combination with fluorouracil, epirubicin and cyclophosphamide (FEC).

In a further aspect, the present invention relates to a method of treatment of cancer, said method comprising, as a first step, stratifying a cancer patient for tumor treatment using the in vitro method as defined above, and, as a second step, providing the selected tumor treatment regimen to the cancer patient. The tumor treatment regimen is selected based on the molecular subtype identified by the in vitro method as defined above.

In one embodiment, said method comprises using quantitative results obtained by the in vitro method as defined above for direct decision-making in favor of or against adjuvant/neoadjuvant chemotherapy.

In yet a further aspect, the present invention relates to a kit useful for identifying a molecular subtype of a tumor in a cancer patient by means of reverse transcription (RT) quantitative PCR, said kit comprising:
  at least one pair of HER2-specific primers and at least one HER2-specific probe;
  at least one pair of ESR1-specific primers and at least one ESR1-specific probe;
  at least one pair of PGR-specific primers and at least one PGR-specific probe; and
  at least one pair of Ki67-specific primers and at least one Ki67-specific probe; and/or
  at least one pair of RACGAP1-specific primers and at least one RACGAP1-specific probe.

In one embodiment, the quantitative PCR is fluorescence-based quantitative real-time PCR.

In one embodiment, detection of the probe is based on amplification-mediated probe displacement.

In one embodiment, the probe is a dual-label probe comprising a fluorescence reporter moiety and a fluorescence quencher moiety.

In one embodiment, the kit further comprises a reverse transcriptase and a DNA polymerase.

In one embodiment, the reverse transcriptase and the polymerase are provided in the form of an enzyme-mix which allows a one-step reverse transcription (RT) quantitative PCR.

In one embodiment, the kit further comprises at least one pair of reference gene-specific primers and at least one reference gene-specific probe. In one embodiment, the reference gene is one or more selected from the group comprising CALM2, B2M, RPL37A, GUSB, HPRT1 and GAPDH, preferably CALM2 and/or B2M.

In one embodiment, the kit further comprises at least one control RNA sample. In one embodiment, the at least one control RNA sample is used as a positive control and/or a control sample (calibrator), wherein, preferably, the at least one control RNA sample comprises synthetic mRNA coding for one or more gene products (or parts thereof) of one or more genes selected from the group comprising HER2, ESR1, PGR, Ki67, RACGAP1 and one or more reference genes. In one embodiment, the one or more reference genes are selected from the group comprising CALM2, B2M, RPL37A, GUSB, HPRT1 and GAPDH, preferably CALM2 and/or B2M.

In one embodiment, the kit may further comprise a DNase and a DNase reaction buffer.

Preferably, the primers and probes are as defined further above in connection with the in vitro method of the present invention.

In one embodiment, the primers provide an amplicon size of less than 120 bp, preferably less than 100 bp.

In one embodiment, the ESR1-specific primers have a length of 15 to 30 nucleotides and comprise at least 10 contiguous nucleotides of the sequences of SEQ ID NOs: 1 and 2, and/or the HER2-specific primers have a length of 15 to 30 nucleotides and comprise at least 10 contiguous nucleotides of the sequences of SEQ ID NOs: 4 and 5, and/or the Ki67-specific primers have a length of 15 to 30 nucleotides and comprise at least 10 contiguous nucleotides of the sequences of SEQ ID NOs: 7 and 8, and/or the PGR-specific primers have a length of 15 to 30 nucleotides and comprise at least 10 contiguous nucleotides of the sequences of SEQ ID NOs: 10 and 11, and/or the RACGAP1-specific primers have a length of 15 to 30 nucleotides and comprise at least 10 contiguous nucleotides of the sequences of SEQ ID NOs: 13 and 14. In one embodiment, the specific primers comprise at least 15 contiguous nucleotides of the sequences indicated above.

In one embodiment, the ESR1-specific primers have the sequences of SEQ ID NOs: 1 and 2, and/or the HER2-specific primers have the sequences of SEQ ID NOs: 4 and 5, and/or the Ki67-specific primers have the sequences of SEQ ID NOs: 7 and 8, and/or the PGR-specific primers have the sequences of SEQ ID NOs: 10 and 11, and/or the RACGAP1-specific primers have a the sequences of SEQ ID NOs: 13 and 14.

In one embodiment, the ESR1-specific probe has a length of 20 to 35 nucleotides and comprises at least 15 contiguous nucleotides of the sequence of SEQ ID NO: 3, and/or the HER2-specific probe has a length of 20 to 35 nucleotides and comprises at least 15 contiguous nucleotides of the sequence of SEQ ID NO: 6, and/or the Ki67-specific probe has a length of 20 to 35 nucleotides and comprises at least 15 contiguous nucleotides of the sequence of SEQ ID NO: 9, and/or the PGR-specific probe has a length of 20 to 35 nucleotides and comprises at least 15 contiguous nucleotides of the sequence of SEQ ID NO: 12, and/or the RACGAP1-specific probe has a length of 20 to 35 nucleotides and comprises at least 15 contiguous nucleotides of the sequence of SEQ ID NO: 15. In one embodiment, the specific probes comprise at least 20 contiguous nucleotides of the sequences indicated above.

In one embodiment, the ESR1-specific probe has the sequence of SEQ ID NO: 3, and/or the HER2-specific probe has the sequence of SEQ ID NO: 6, and/or the Ki67-specific probe has the sequence of SEQ ID NO: 9, and/or the PGR-specific probe has the sequence of SEQ ID NO: 12, and/or the RACGAP1-specific probe has the sequence of SEQ ID NO: 15.

Preferably, the probes as defined above are dual-label probes comprising a fluorescence reporter moiety and a fluorescence quencher moiety.

In one embodiment, the tumor is a solid tumor. In one embodiment, the tumor is a breast tumor or is derived from a breast tumor (e.g. by metastasis). In one embodiment, the cancer is breast cancer.

As used herein, the term "kit of parts (in short: kit)" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents such as dNTPs. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in the methods of the invention. The data carrier may comprise a threshold value or reference level of RNA transcript, e.g., mRNA. In case that the data carrier comprises an access code which allows the access to a database, said threshold value or reference level is deposited in this database. In addition, the data carrier may comprise information or instructions on how to carry out the methods of the present invention.

In another aspect, the present invention relates to the use of a kit as defined above for identifying a molecular subtype of a tumor in a cancer patient.

In another aspect, the present invention relates to the use of a kit as defined above for assessing a cancer patient's risk for distant metastasis.

The present invention overcomes major disadvantages of the current standard and state of the art diagnostic method immunohistochemistry and more recent methods.

The present invention allows reliable molecular subtyping of tumors, in particular breast tumors, which then allows the medical practitioner to select the most suitable tumor treatment regimen.

Thanks to the preferred order of the assessment of the four or five markers (preferably, the expression level of RNA transcript of HER2 is determined first) there is no misclassification of HER2-positive into luminal A and B subtypes, a problem that often occurs if the subtyping is based on hierarchal cluster analysis or correlation analysis (Peron et al. (2000), Nature, 406:747-752; TCGA (Cancer Genome Atlas Network) (2012), Nature, 490:61-70). Furthermore, there is no misclassification of false-positive and clinically HER2-negative tumors, which, according to Perou et al., may occur in up to 30% of these cases.

The present invention provides methods and kits to confirm/reassess uncertain or contradictory results of an immunochemical analysis, especially in the following breast cancer patient groups as identified by IHC: ESR1/PGR negative (approx. 30% of all breast cancer patients), ESR1/PGR weakly positive (approx. 15% of all breast cancer patients), HER2 3+ (tumor biopsy IHC, not confirmed by dissection tumor IHC; approx. 15% of all breast cancer patients) and HER 2+ (approx. 20% of all breast cancer patients).

The methods and kits of the present invention facilitate direct decision-making in favor of or against adjuvant/neoadjuvant chemotherapy in luminal breast cancer due to the distinction of luminal A and luminal B subtypes by reliable detection of Ki67- and/or RACGAP1 RNA transcript. This is particularly helpful for patients having ESR1/PGR positive and up to grade 2 tumors (approx. 50% of all breast cancer patients).

The present invention allows a distinction of luminal A and luminal B tumors with clearly differing overall survival and distant metastasis free survival rates. While luminal B patients have a continuously high risk of metastasis, particularly in the first five years after treatment (e.g. surgery), the risk of luminal A patients is constantly and clearly lower. Thus, the methods and kits also allow for the assessment of a patient's risk for distant metastasis.

By using the methods of the present invention, approximately 77% of the luminal tumors in the FinHER study (Joensuu et al. (2006), N Engl J Med, 354:809-820) are allocated to the low risk group luminal A, and there are no intermediate risk groups. Furthermore, the classification into luminal A and luminal B reduces the significance of histological grading and nodal status, two parameters that are usually very important for tumor prognosis. Therefore, uncertainties regarding the therapy of grade 2 tumors are resolved in a clinically relevant manner.

The methods and kits of the present invention also allow for the prediction of response to systemic therapy thanks to the quantitative determination of the RNA transcript expression level of ESR1, HER2, Ki67 and, optionally, RACGAP1. This is particularly helpful for patients having invasive breast cancer>1 cm with uncertain IHC (approx. 40% of all breast cancer patients).

Novelties of the present invention include not only the mRNA-based estimation of breast cancer biomarkers, but also the algorithmic definition of subtypes. The inclusion of mandatory PGR positivity for luminal A definition in addition to low Ki67 is an original criterion, not included in the 2011 St. Gallen clinical guidelines at the time of the invention. In addition, tumors displaying HER2 mRNA expression exceeding the predefined cut-off are classified as HER2-positives irrespective of ESR1/PGR status which also deviates from the 2011 international guidelines, which are still in effect. All these new aspects contribute to the predictive value of the RT-qPCR-based approach and kit of the present invention. In fact, these novelties, technical in terms of RT-qPCR-based biomarker estimation and theoretical in terms of the classification algorithm, provide a more accurate and meaningful subtyping of patients in the FinHer clinical trial, which ultimately provides a predictive tool for docetaxel benefit in an adjuvant therapy setting.

Figure 1:
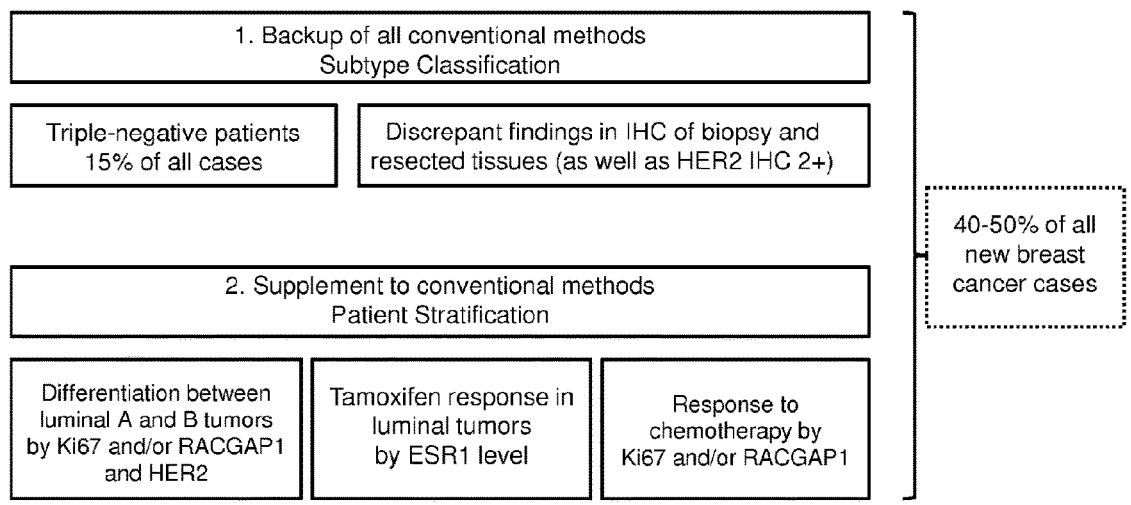
FIG. 1 outlines potential uses for the methods of the present invention as a back up for conventional methods of subtype classification (e.g. THC) and as a supplement to conventional methods of patient stratification.

Taken together, the present invention serves currently largely unmet clinical needs for a reliable, reproducible and quantitative assessment of prognosis and prediction of therapy success in at least 50% of all breast cancer patients (see also FIG. 1).

The present invention is further illustrated by the following examples which are not be construed as limiting the scope of the invention.

EXAMPLES

Example 1

Determination of mRNA Expression Levels by Reverse Transcription (RT) Quantitative PCR (RT-qPCR)

RNA was isolated from paraffin-embedded, formalin-fixed tissues (=FFPE tissues). More particularly, total RNA from a 5 to 10 μm curl of FFPE tumor tissue was extracted using the High Pure RNA Paraffin Kit (Roche, Basel, Switzerland) or the XTRAKT RNA Extraction Kit XL (Stratifyer Molecular Pathology, Cologne, Germany), quantified by the Ribogreen RNA Quantitation Assay (Molecular Probes, Eugene, Oreg.) and qualified by real-time fluorescence RT-PCR of a fragment of the reference gene RPL37A. It was recognized that differences exist between different extraction technologies when comparing quantitative data of target genes of sequential slices by different methodologies. For the purpose of the present invention the use of the XTRAKT RNA Extraction Kit XL was preferred. In general 2.5 μl RNA of each qualified extraction (approx. 50-100 ng) was assayed by qRT-PCR as described below.

For a detailed analysis of gene expression by quantitative RT-PCR methods, primers flanking the region of interest and a fluorescent labeled probe hybridizing in-between were utilized. Target specific primers and probes were selected using the NCBI prime designing tool (www.ncbi.nlm.nih.go). RNA specific primer/probe sequences were used to enable RNA specific measurements by locating primer/probe sequences across exon/exon boundaries.

Furthermore, primer/probes were selected not to bind to sequence regions with known polymorphisms (SNPs). In case multiple isoforms of the same gene exist, primers were selected to amplify all relevant splice variants. All primer pairs were checked for specificity by conventional PCR reactions. After further optimization of the primers/probes, the primers and probes listed in Table 1 gave the best results. These primers/probes are superior to primers/probes known from the prior art, e.g. in terms of specificity and amplification efficiency. To standardize the amount of sample RNA, the genes CALM2 and B2M were selected as reference genes, since they were not differentially regulated in the samples analyzed.

TABLE 1

| Name | Sequence (5'→3') | Purification | 5' Modification | 3' Modification |
|---|---|---|---|---|
| ESR_F | AGAGGGTGCCAGGCTTTGT (SEQ ID NO: 1) | HPLC | none | none |
| ESR_R | AGGATCTCTAGCCAGGCACATT (SEQ ID NO: 2) | HPLC | none | none |
| ESR_P | TTTGACCCTCCATGATCAGGTCCACCT (SEQ ID NO: 3) | HPLC | JOE | TAMRA |
| HER2_F | GAACTCACCTACCTGCCCACC (SEQ ID NO: 4) | HPLC | none | none |
| HER2_R | GACCTGCCTCACTTGaTTGTG (SEQ ID NO: 5) | HPLC | none | none |
| HER2_P | CCAGGAGGTGCAGGGCTACGTG (SEQ ID NO: 6) | HPLC | 6-FAM | Dabcyl |
| KI67_F | CGAGACGCCTGGTTACTATCAA (SEQ ID NO: 7) | HPLC | none | none |
| KI67_R | GGATACGGATGTCACATTCAATACC (SEQ ID NO: 8) | HPLC | none | none |
| KI67_P | ACGGTCCCCACTTTCCCCTGAGC (SEQ ID NO: 9) | HPLC | 6-FAM | Dabcyl |
| PGR_F | AAACTTCTTGATAACTTGCATGATCTT (SEQ ID NO: 10) | HPLC | none | none |
| PGR_R | CAATAACTTCAGACATCATTTCTGG (SEQ ID NO: 11) | HPLC | none | none |
| PGR_P | CGGGACTGGATAAATGTATTCAAGCAGTAC (SEQ ID NO: 12) | HPLC | 6-FAM | Dabcyl |

TABLE 1 -continued

Used primers and probes.

| Name | Sequence (5'→3') | Purification | 5' Modification | 3' Modification |
|---|---|---|---|---|
| RAC_F | GAATGTGCGGAATCTGTTTGAG (SEQ ID NO: 13) | HPLC | none | none |
| RAC_R | TCGCCAACTGGATAAATTGGA (SEQ ID NO: 14) | HPLC | none | none |
| RAC_P | ACTGAGAATCTCCACCCGGCGCA (SEQ ID NO: 15) | HPLC | JOE | TAMRA |
| B2M_F | GTATGCCTGCCGTGTGAACC (SEQ ID NO: 16) | HPLC | none | none |
| B2M_R | GGCATCTTCAAACCTCCATGAT (SEQ ID NO: 17) | HPLC | none | none |
| B2M_P | AGTGGGATCGAGACATGTAAGCAGC (SEQ ID NO: 18) | HPLC | JOE | TAMRA |
| CALM2_F | AGGAGGCGAATTAGTCCGA (SEQ ID NO: 19) | HPLC | none | none |
| CALM2_R | GCTCTTCAGTCAGTTGGTCA (SEQ ID NO: 20) | HPLC | none | none |
| CALM2_P | TCGCGTCTCGGAAACCGGTAGC (SEQ ID NO: 21) | HPLC | JOE | TAMRA |

TaqMan® validation experiments were performed showing that the efficiencies of the target and the control amplifications are approximately equal which is a prerequisite for the relative quantification of gene expression by the comparative ΔCT method. To perform the expression analysis of genes of interest within a biological sample, 4×duplex assay-mixtures were prepared by mixing the respective primer/probes of two specific assays. For separate detection of CT values the assay probes were modified with different fluorescent probes. Each 4×assay-mix contained 2 µM of unmodified forward and reverse primer and 1.2 µM of probe. For each reaction 2.5 µl total RNA extracted from FFPE sections (see above) was mixed with 2.5 µl assays-mix, 2.5 µl enzyme-mix and 2.5 µl water in one well of a 96-well-Optical Reaction Plate. Measurements of the PCR reaction were done according to the instructions of the manufacturer with a Versant kPCR Cycler (Siemens) or a Light Cycler 480 (Roche) under appropriate conditions (5 min. 50° C., 20 sec. 95° C., 15 sec. 95° C., 1 min. 60° C.; 40 cycles). Prior to the measurement of so far unclassified biological samples control, experiments with, e.g., cell lines, healthy control samples, samples of defined molecular tumor subtypes can be used for standardization of the experimental conditions.

Example 2

Molecular Subtyping of Tumors Based on the mRNA Expression Levels of HER2 ESR1, PGR, Ki67 and, Optionally, RACGAP1

For the evaluation of breast tumors, 855 out of 1010 breast cancer patients of the FinHER study (Joensuu et al. (2006), N Engl J Med, 354:809-820) could be used. The mean cut-off values (given as 40-ΔCT values) were as follows: HER2: 38; ESR1: 34; PGR: 30,2; Ki67: 31.7; and RACGAP1: 34.2. The cut-off values for HER2 and ESR1 were determined based on evaluation of previous studies (Koutras et al. (2008), Brit. J. of Canc., 99:1775-1785; Pentheroudakis et al. (2009), Breast Cancer Res Treat 2009, 116:131-143) using 268 samples and were applied to the FinHER study (proportional hazards model validation). CALM2 served as reference gene.

Based on the mRNA expression level of HER2, ESR1, PGR and Ki67 (neg/low indicates an expression level which is lower than the defined expression threshold; pos/increased indicates an expression level which is higher than the defined expression threshold) tumors are allocated to the molecular subtypes HER2-positive luminal A (LumA), luminal B (LumB) and triple-negative (TNT). As shown in Table 2, the molecular subtyping of tumors in accordance with the present invention differs from those that are based on prior art methods, e.g., immunohistochemistry (Goldhirsch et al. (2011), Annals of Oncology, 22:1736-1747, St. Gallen International Expert Consensus on the Primary Therapy of Early Breast Cancer 2011) and analysis of only three gene markers (Sotiriou et al. (2009), N Engl J Med, 360(8):790-800).

TABLE 2

Molecular subtyping of tumors.

| HER2 | ESR1 | PGR | Ki67 | Present Invention | Goldhirsch et al. (2011) | Sotiriou et al. (2009) |
|---|---|---|---|---|---|---|
| neg | neg | neg | low | TNT | TNT | basal-like |
| neg | neg | neg | increased | TNT | TNT | basal-like |
| neg | pos | pos | low | LumA | LumA | LumA |
| neg | neg | pos | low | LumA | LumA | LumB |
| neg | neg | pos | increased | LumB | LumA | LumB |
| neg | pos | pos | low | LumB | LumA | LumB |
| neg | pos | pos | increased | LumB | LumA | LumB |
| neg | pos | neg | increased | LumB | LumA | LumB |
| pos | pos | pos | increased | HER2 | LumB | HER2 |
| pos | pos | pos | low | HER2 | LumB | HER2 |

TABLE 2-continued

Molecular subtyping of tumors.

| HER2 | ESR1 | PGR | Ki67 | Present Invention | Goldhirsch et al. (2011) | Sotiriou et al. (2009) |
|---|---|---|---|---|---|---|
| pos | pos | neg | low | HER2 | LumB | HER2 |
| pos | neg | neg | low | HER2 | HER2 | HER2 |
| pos | neg | neg | increased | HER2 | HER2 | HER2 |

Figure 2:
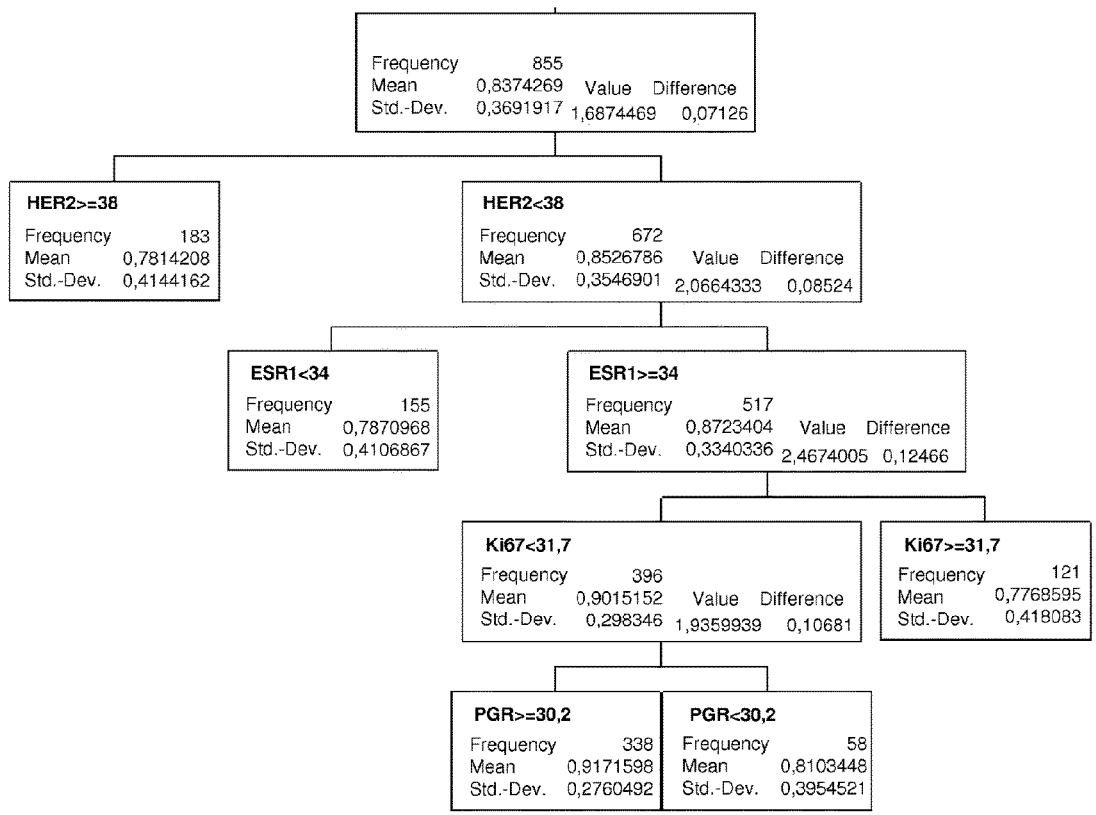
FIG. 2 depicts a partitioning test to evaluate the prognostic and predictive value of the expression level of HER2, ESR1, PGR, Ki67 and RACGAP1 mRNA for the 5-years survival rate of breast cancer patients. Available data from 855 tumors were first stratified by HER2 mRNA expression level to identify HER2-positive tumors (≥cut-off value 38). HER2-negative tumors were further stratified by ESR1 mRNA expression level. A: ESR1-positive tumors (≥cut-off value 34) were further stratified by Ki67 mRNA expression level (cut-off value 31.7) followed by PGR mRNA expression level (cut-off value 30.2). B: Alternatively, ESR1-positive tumors (≥cut-off value 34) were further stratified by PGR mRNA expression level (cut-off value 30.2) followed Ki67 snRNA expression level (cut-off value 31.7). Kaplan-Meier analyses of these data are shown in FIGS. 3 and 4. C: Ki67-positive and Ki67-negative tumors were stratified by RACGAP1 mRNA expression level (cut-off value 34.2). To improve the number of patients for further analysis of RACGAP1, no data for PGR are given in the picture. The further consideration of PGR does not alter the overall outcome with respect to CGAP1. The data (see Table 3) shows that RACGAP1 mRNA expression levels below or above the defined threshold are associated with particularly significant differences in the 5-years survival rate.
Figure 2:
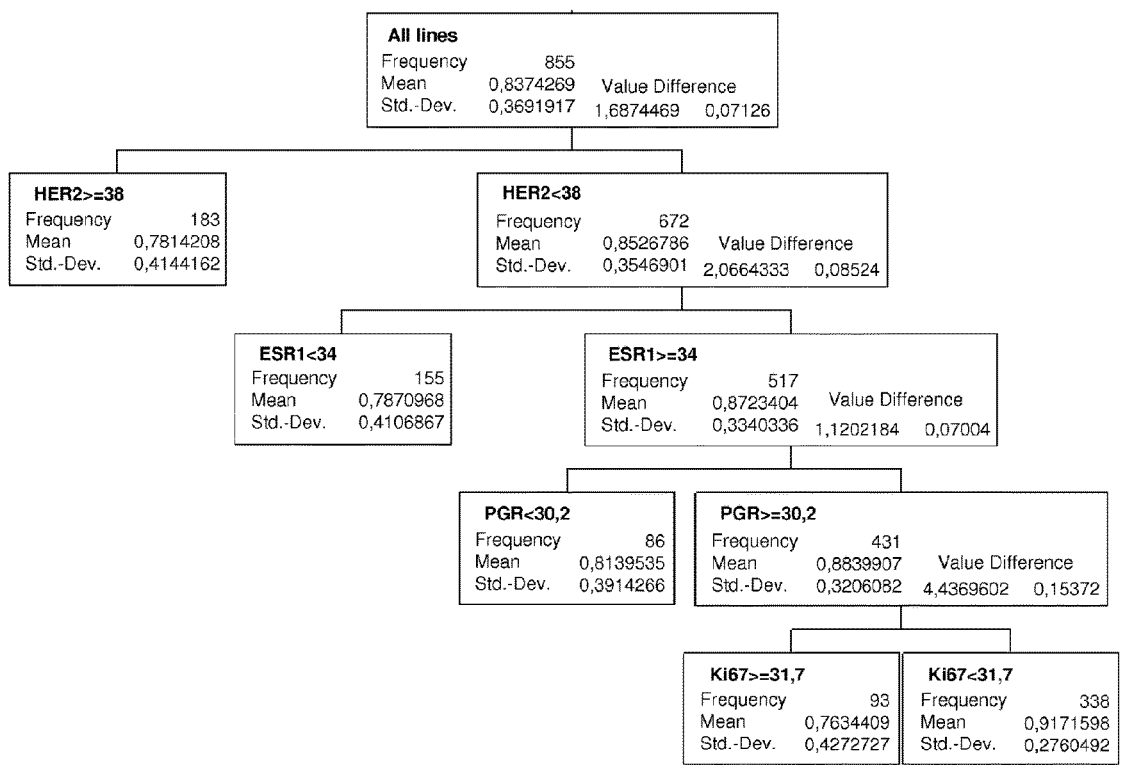
Figure 2:
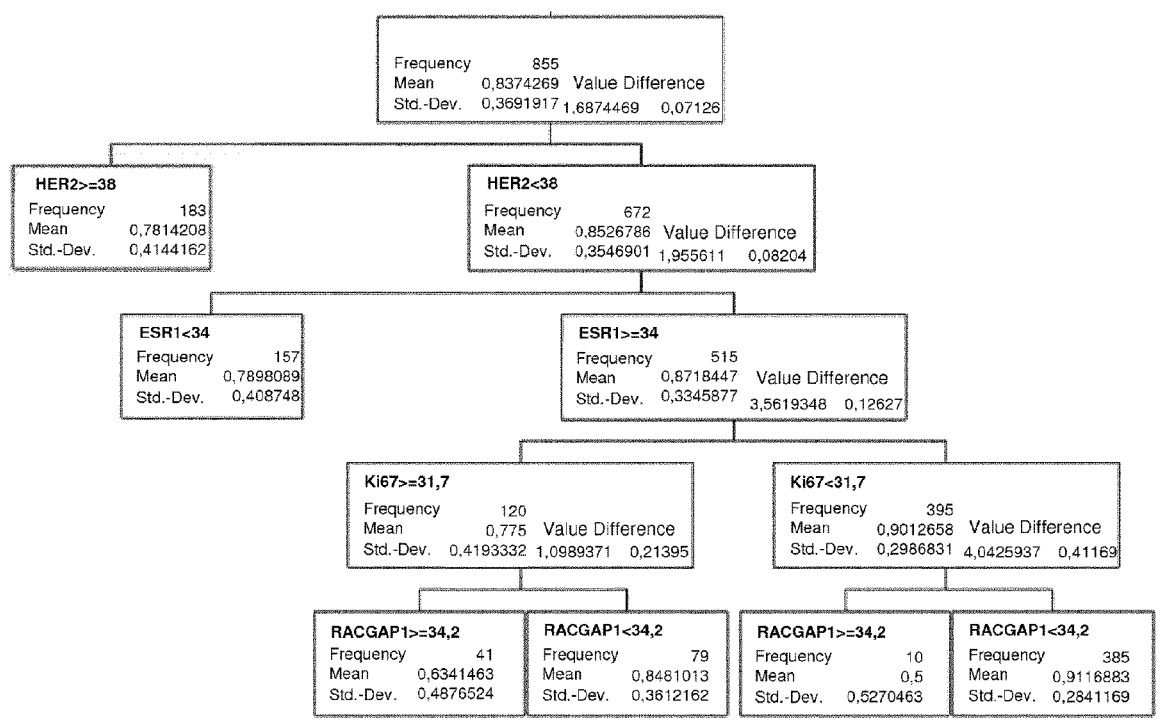

FIG. 2 shows a partitioning test to evaluate the prognostic and predictive value of the expression level of HER2, ESR1, PGR, Ki67 and RACGAP1 mRNA for the 5-years survival rate of breast cancer patients. These data show that RAC-GAP1 mRNA expression levels below or above the defined threshold are associated with particularly significant differences in the 5-years survival rate. More particularly, an increased level of RACGAP1 mRNA expression reduces the probability of survival significantly. Probability of survival is further reduced if the mRNA expression of RACGAP1 is increased and Ki67 mRNA expression is low (see Table 3). With current analytical procedures, these risk patients (who would require a different kind of follow-up care, e.g., examination with particular imaging methods) remain undiscovered.

TABLE 3

RACGAP1/Ki67 mRNA expression and probability of survival.

| Ki67 | RACGAP1 | 5-years Survival |
|---|---|---|
| increased | increased | 50% |
| increased | low | 84% |
| low | increased | 63% |
| low | low | 91% |
| increased | unaccounted | 78% |
| low | unaccounted | 90% |

Figure 3:
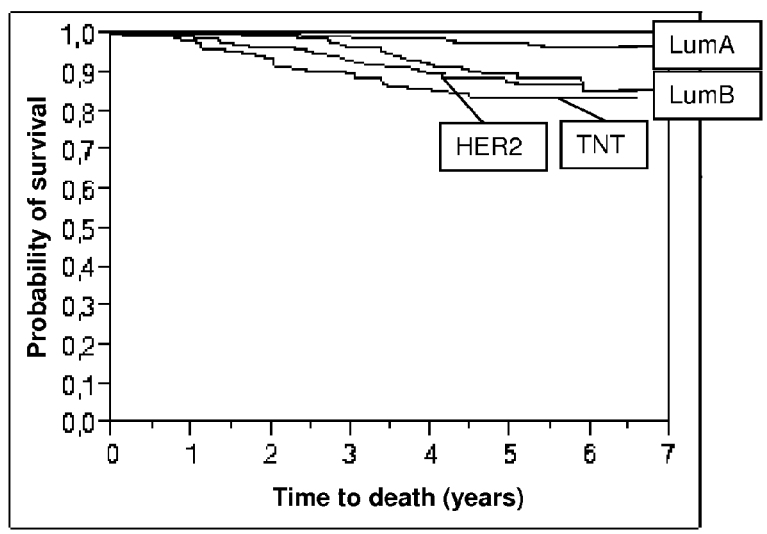
FIG. 3 depicts a Kaplan Meier analysis of survival of breast cancer patients with HER2-positive (HER2), luminal A (LumA), luminal B (LumB) or triple-negative (TNT) tumors, wherein the molecular subtype of the tumor was identified in accordance with the present invention, based on the mRNA expression levels of HER2, ESR1, PGR and Ki67. The luminal A subtype, as defined by the present inventors, is associated with an overall survival rate of 97% after 5 years (vs. 87% for luminal B and HER2-positive tumors and 84% for triple-negative tumors).

Using Kaplan Meier analysis the inventors analyzed the survival of patients with HER2-positive, luminal A, luminal B and triple-negative tumors, respectively, wherein the molecular subtype of the tumor was identified in accordance with the present invention, i.e. based on the mRNA expression levels of HER2, ESR1, PGR and Ki67. As shown in FIG. 3, the luminal A subtype, as defined by the present inventors, is associated with an overall survival rate of 97% after 5 years (vs. 87% for luminal B and HER2-positive tumors and 84% for triple-negative tumors).

Figure 4:
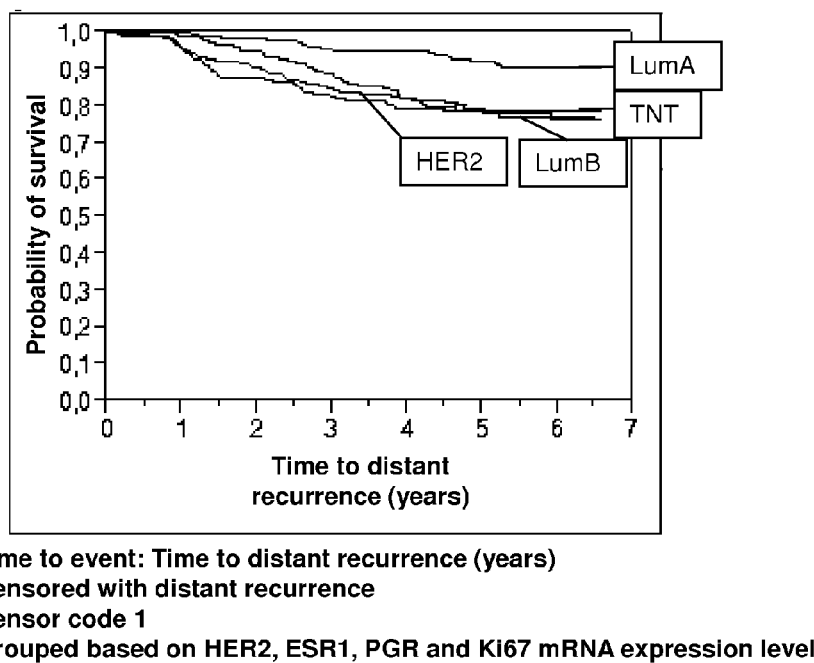
FIG. 4 depicts a Kaplan Meier analysis of distant metastasis free survival ("DMFS"; distant recurrence X years after surgery) of breast cancer patients with HER2-positive (HER2), luminal A (LumA), luminal B (LumB) or triple-negative (TNT) tumors, wherein the molecular subtype of the tumor was identified in accordance with the present invention, based on the mRNA expression levels of HER2, ESR1, PGR and Ki67. The luminal A subtype, as defined by the present inventors, is associated with a DMFS rate of 92% after 5 years (vs. 78% for luminal B, HER2-positive and triple-negative tumors).
Figure 6:
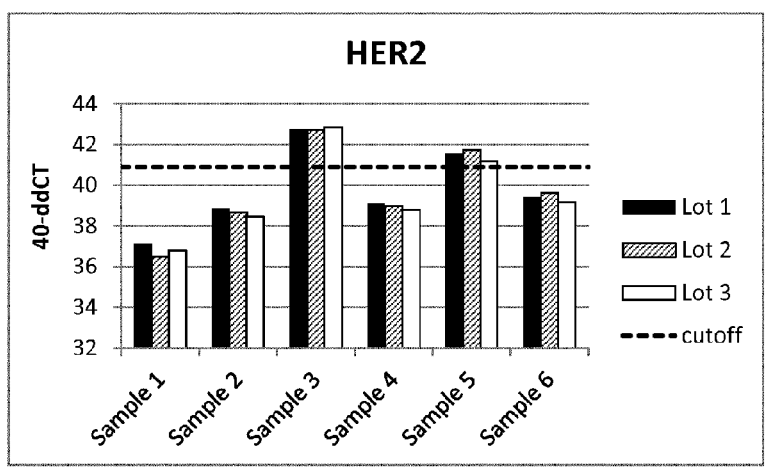
FIGS. 6 to 9 show the 40-ΔΔCT values of the markers HER2, ESR1, PGR and Ki67 as determined by RT-qPCR for patient samples 1 to 6 and lots 1 to 3.
Figure 7:
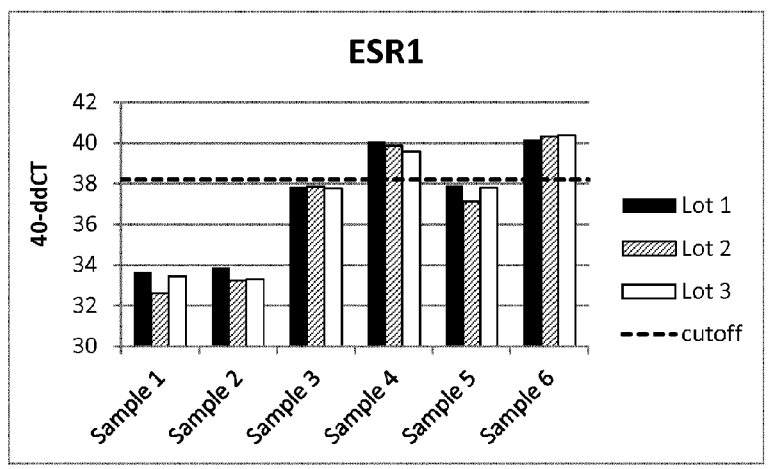
Figure 8:
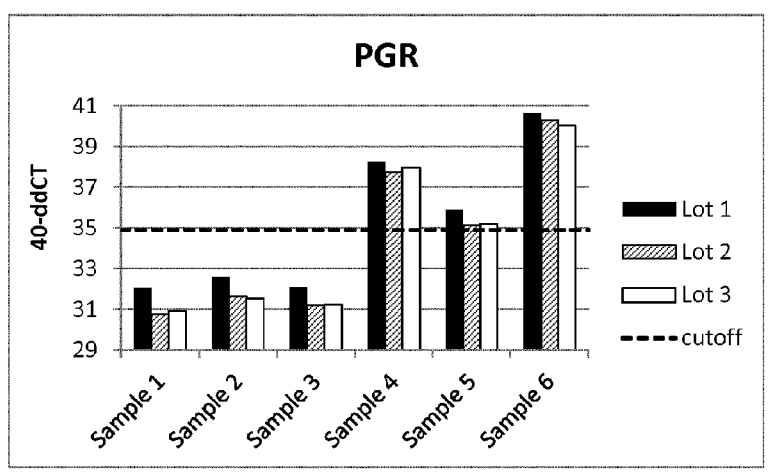
Figure 9:
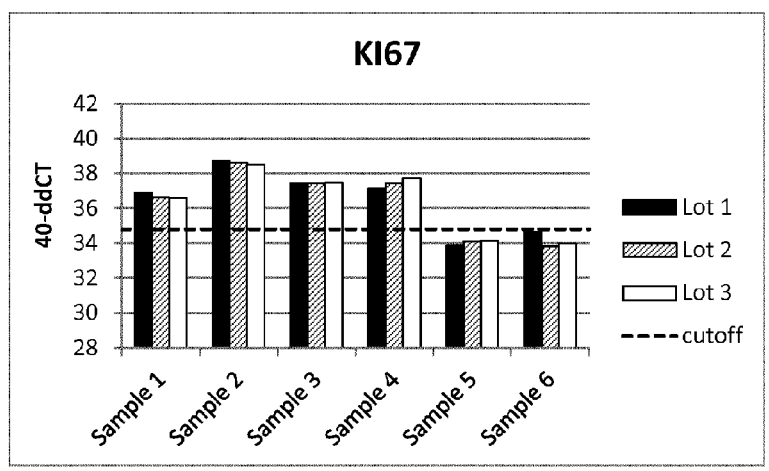
Figure 10:
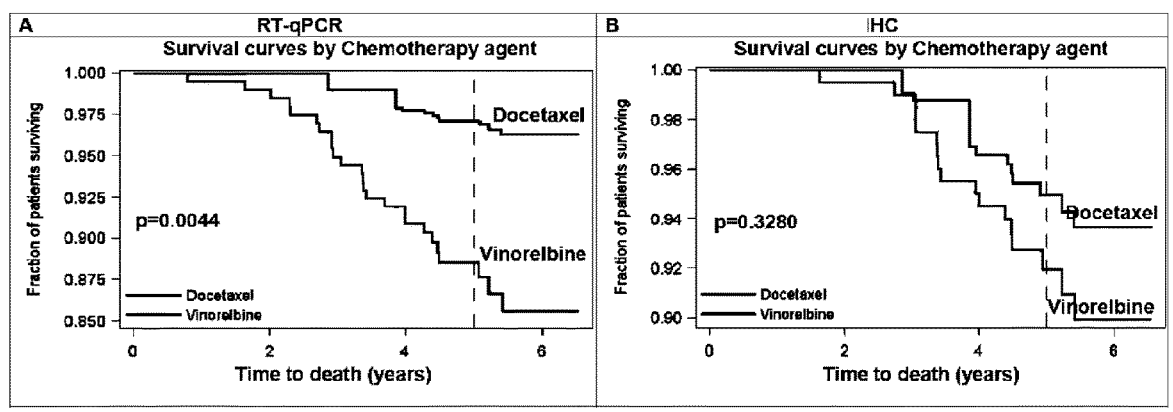
FIG. 10 depicts a Kaplan Meier analysis of the overall survival of patients with luminal B tumors. A: When defined by RT-qPCR, patients with luminal B cancer treated with docetaxel-FEC survive significantly longer than when treated with vinorelbine-FEC (97% vs. 89% respectively, Hazard Ratio [HR] 0.241; CI: 0.090-0.642). B: en the tumor subtype is defined by IHC, the benefit of docetaxel for luminal B patients cannot be shown (95% vs. 92%, HR 0.617; CI 0.235-1.623).
Figure 11:
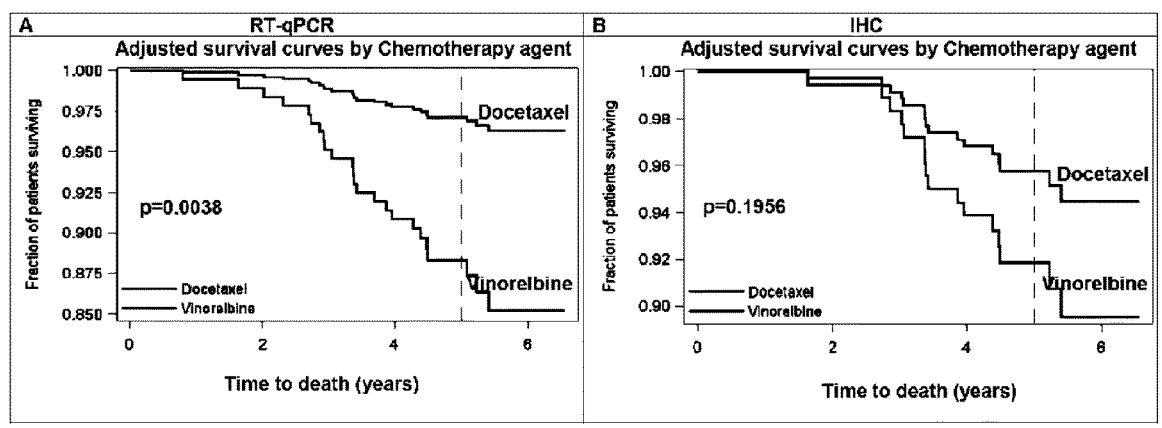
FIG. 11 depicts a Kaplan Meier analysis of the overall survival of patients with luminal B tumors, adjusted for tumor histologic type by Cox Regression as specified in the SAP. A: The prediction of the docetaxel benefit by RT-qPCR kit remains significant (97% vs. 88%, HR 0.232; CI 0.087-0.624). B: Subtyping by IHC is not predictive for a docetaxel benefit (96% vs. 92%, HR 0.510; CI 0.184-1.414).
Figure 12:
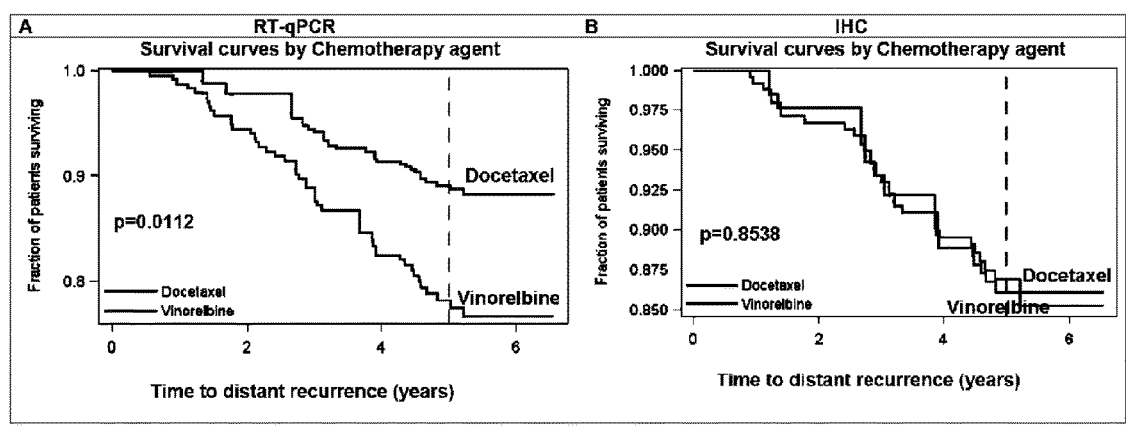
FIG. 12 depicts a Kaplan Meier analysis of distant metastasis free survival (DMFS) of luminal B tumor patients. A: When defined by RT-qPCR, luminal B patients have a higher probability to remain free of distant metastasis when treated with docetaxel-FEC as compared to vinorelbine-FEC (89% vs. 78% respectively, HR 0.471; CI 0.263-0.843). B: When luminal B tumors are defined by IHC, survival differences are not observed between different treatment regimens (87% vs. 86%, HR 0.938 CI 0.474-1.856).
Figure 13:
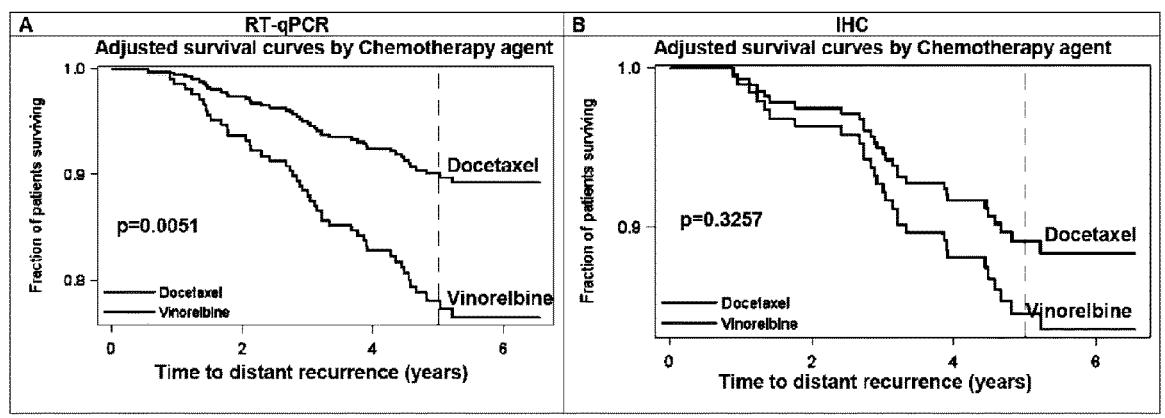
FIG. 13 depicts a Kaplan Meier analysis of distant metastasis free survival of patients with luminal B tumors, adjusted for number of metastatic lymph nodes, tumor size and histologic type by Cox Regression as specified in the SAP. A: By using the subtyping assay of the present invention the effect remains significant (90 vs. 78%, HR 0.409; CI 0.219-0.764). B: By contrast there is no effect when tumor subtyping occurs by IHC (89% vs. 85%, HR 0.674; CI 0.307-1.481).
Figure 14:
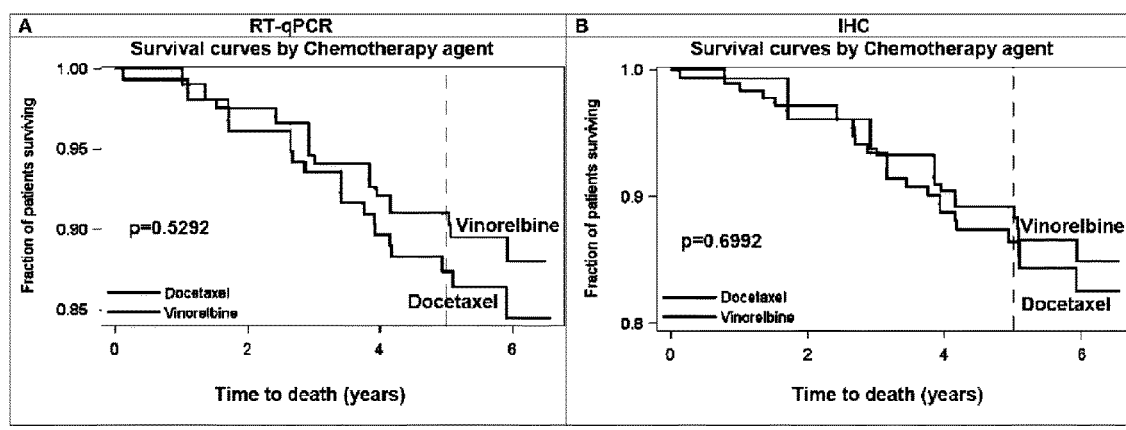
FIG. 14 depicts a Kaplan Meier analysis of the overall survival of HER2-positive tumor patients. A: en defined by RT-qPCR, HER2-positive patients do not have better overall survival rates when treated with docetaxel as compared to vinorelbine (87 vs. 91%, HR 1.320; CI 0.556-3.132). B.

The inventors further analyzed distant metastasis free survival ("DMFS"; distant recurrence X years after surgery) of patients with HER2-positive, luminal A, luminal B and triple-negative tumors, respectively, wherein the molecular subtype of the tumor was identified in accordance with the present invention. As shown in FIG. 4, the luminal A subtype, as defined by the present inventors, is associated with a distant metastasis free survival rate of 92% after 5 years (vs. 78% for luminal B, HER2-positive and triple-negative tumors).

In a multivariate analysis of overall survival with the most important histopathological standard parameters (tumor size, nodal status and histological grading) the molecular subtyping in accordance with the present invention turned out to be highly significant, whereas both histological grading and nodal status lost their significance.

Finally, a multivariate Cox regression analysis of DMFS comparing the molecular subtyping by immunohistochemistry (Sotiriou et al. (2009), N Engl J Med, 360(8):790-800) with the molecular subtyping by the method in accordance with the present invention, based on the mRNA expression levels of HER2, ESR1, PGR and Ki67, was performed (FIG. 5). The analysis clearly shows the superiority of the method of the present invention, as the immunohistochemical subtyping looses its significance when the results obtained by the method of the present invention are included in the Cox proportional hazards model.

Example 3

Measurement of mRNA Expression Levels of Biomarkers HER2, ESR1, PGR, Ki67 by Reverse Transcription (RT) Quantitative PCR (RT-qPCR) and Molecular Subtype Determination RNA was isolated from FFPE tissues. More particularly, total RNA from 10 µm sections of FFPE breast tumor tissue were extracted using the XTRAKT RNA Extraction Kit (Stratifyer Molecular Pathology, Cologne, Germany). RNA eluates were directly used without determination of concentration. 2.5 µl A of each extraction was assayed by RT-qPCR as described below.

For RT-qPCR, primers flanking the region of interest and a 5'-fluorescently labeled hydrolysis probe with a 3'-TAMRA or -Dabcyl Quencher were used for each target. Primers and probes used are listed in Table 1. To correct for different amounts of sample RNA, the genes CALM2 and B2M were used as reference genes for normalization of expression results. RT-qPCR was performed in duplexes in the following combinations, HER2/ESR1, Ki67/B2M and PGR/CALM2. Each of the three 4× assay mixes contained 2 µM of unmodified forward and reverse primer and 1.2 µM of probe. For each assay, a master mix with 2.5 µl assay-mix, 2.5 µl 4× enzyme-mix (TaqManFast Virus 1-Step Master-Mix, Life Technologies), and 2.5 µl water per reaction was prepared and 7.5 µl of each master mix distributed into a kPCR 96-well reaction plate in triplicates. 2.5 µl total RNA extracted from FFPE sections (see above) or, alternatively, positive (IVT RNA) or negative control (water) was added to each well. Analysis of RNA eluates derived from three patient samples was done with three lots of assay mixes and enzyme mixes. Measurement of the 1-step RT-qPCR reactions was done according to the instructions of the manufacturer with a Versant kPCR Cycler (Siemens) with the following thermal profile: 5 min 50° C., 20 sec 95° C. one cycle each and 15 sec 95° C., 1 min 60° C. for 40 cycles.

6 patient samples along with the positive and negative controls were analyzed with three lots of assay mixes. 40-ΔΔCT values were calculated according to the description given above (calculation method 4). FIGS. 6 to 9 show the 40-ΔΔCT values for each marker, for each sample and lot. The cut-off values (given as 40-ΔΔCT values) for the classification of the biomarkers in positive or negative were as follows: HER2: 40.90; ESR1: 38.20; PGR: 34.90; Ki67: 34.80. The molecular subtype was defined as shown in Table 4.

TABLE 4

Molecular subtyping of patient samples.

| HER2 | ESR1 | PGR | KI67 | Subtype |
|------|------|-----|------|---------|
| pos | pos | pos | pos | HER2+ |
| pos | pos | pos | neg | HER2+ |
| pos | pos | neg | neg | HER2+ |
| pos | neg | pos | neg | HER2+ |
| pos | neg | pos | pos | HER2+ |
| pos | pos | neg | pos | HER2+ |
| pos | neg | neg | pos | HER2+ |
| pos | neg | neg | neg | HER2+ |
| neg | pos | pos | pos | Luminal-B |
| neg | pos | pos | neg | Luminal-A |
| neg | pos | neg | neg | Luminal-B |
| neg | neg | pos | neg | Luminal-A |
| neg | neg | pos | pos | Luminal-B |
| neg | pos | neg | pos | Luminal-B |
| neg | neg | neg | pos | Triple negative |
| neg | neg | neg | neg | Triple negative |

TABLE 5

40-ΔΔCT values and subtype calling for assay mix lot 1.

| Lot 1 | HER2 | ESR1 | PGR | KI67 | HER2 | ESR1 | PGR | KI67 | Subtype |
|-------|------|------|-----|------|------|------|-----|------|---------|
| Sample 1 | 37.13 | 33.64 | 32.05 | 36.90 | neg | neg | neg | pos | TNBC |
| Sample 2 | 38.86 | 33.86 | 32.60 | 38.72 | neg | neg | neg | pos | TNBC |
| Sample 3 | 42.75 | 37.84 | 32.08 | 37.43 | pos | neg | neg | pos | HER2+ |
| Sample 4 | 39.11 | 40.07 | 38.22 | 37.13 | neg | pos | pos | pos | LumB |
| Sample 5 | 41.55 | 37.87 | 35.89 | 33.85 | pos | neg | pos | neg | HER2+ |
| Sample 6 | 39.40 | 40.14 | 40.63 | 34.64 | neg | pos | pos | neg | LumA |

TABLE 6

40-ΔΔCT values and subtype calling for assay mix lot 2.

| Lot 2 | HER2 | ESR1 | PGR | KI67 | HER2 | ESR1 | PGR | KI67 | Subtype |
|-------|------|------|-----|------|------|------|-----|------|---------|
| Sample 1 | 36.49 | 32.61 | 30.77 | 36.61 | neg | neg | neg | pos | TNBC |
| Sample 2 | 38.66 | 33.24 | 31.62 | 38.60 | neg | neg | neg | pos | TNBC |
| Sample 3 | 42.71 | 37.85 | 31.19 | 37.44 | pos | neg | neg | pos | HER2+ |
| Sample 4 | 38.98 | 39.84 | 37.73 | 37.43 | neg | pos | pos | pos | LumB |
| Sample 5 | 41.72 | 37.13 | 35.12 | 34.08 | pos | neg | pos | neg | HER2+ |
| Sample 6 | 39.63 | 40.32 | 40.30 | 33.83 | neg | pos | pos | neg | LumA |

TABLE 7

40-ΔΔCT values and subtype calling for assay mix lot 3.

| Lot 3 | HER2 | ESR1 | PGR | KI67 | HER2 | ESR1 | PGR | KI67 | Subtype |
|-------|------|------|-----|------|------|------|-----|------|---------|
| Sample 1 | 36.77 | 33.46 | 30.90 | 36.60 | neg | neg | neg | pos | TNBC |
| Sample 2 | 38.46 | 33.27 | 31.52 | 38.51 | neg | neg | neg | pos | TNBC |
| Sample 3 | 42.84 | 37.78 | 31.22 | 37.44 | pos | neg | neg | pos | HER2+ |
| Sample 4 | 38.78 | 39.56 | 37.97 | 37.73 | neg | pos | pos | pos | LumB |
| Sample 5 | 41.17 | 37.79 | 35.18 | 34.13 | pos | neg | pos | neg | HER2+ |
| Sample 6 | 39.16 | 40.36 | 40.01 | 33.96 | neg | pos | pos | neg | LumA |

Only slight differences of the results between different reagent lots can be observed. Assay performance was very robust and reproducible for all markers. Tables 5 to 7 show the 40-ΔΔCT values and the positive or negative result for each marker and the translation into the respective subtype as defined in Table 4 (see also Table 2). Marker results (pos/neg) and subtypes were consistent for all 6 samples measured with three different reagent lots.

Example 4

Comparison of Breast Cancer Subtyping by RT-qPCR and IHC in Terms of the Clinical Outcome FIGS. 10 to 19 depict Kaplan-Meier survival curves for different tumor subtypes (luminal B, HER2-positive, luminal A, and triple-negative breast cancer [TNBC]) treated with different chemotherapy agents (docetaxel or vinorelbine). Subytpes defined by RT-qPCR according to the present invention are shown in panel A, whereas subtypes defined by IHC are shown in panel B. Dotted lines mark the 5 year time point for outcome calculations.

The data presented in FIGS. 10 to 19 collectively highlight the superiority of the novel RNA-based classification of breast cancer by RT-qPCR as compared to the conventional protein-based IHC. The data indicate a significant benefit of docetaxel treatment for luminal B tumors. In contrast, IHC-based subtyping failed to show a significant benefit in any subtype with some trends in luminal A, luminal B and triple-negative breast cancer patients. However, as these 3 subtypes comprise ~80% of all patients, the IHC-based subtyping did not provide any clinically useful predictive information.

Importantly, RT-qPCR-defined patients with luminal B tumors derive a statistically significant and exclusive benefit from docetaxel as compared to vinorelbine upon combined treatment with fluorouracil, epirubicin and cyclophosphamide (FEC). These patients remain free of metastasis and live significantly longer when treated with docetaxel, whereas their outcome is clearly worse when receiving vinorelbine. This difference in outcome between the two chemotherapeutic regimens is not observed in any other subtype except for luminal B. Interestingly, docetaxel appears to be even inferior to vinorelbine for luminal A tumors. Although this effect does not reach statistical significance, it clearly excludes a possible beneficial effect of docetaxel treatment in luminal A patients as it is seen in luminal B patients identified by RT-qPCR.

In contrast, when patients are subtyped by IHC, the effect exerted on clinical outcome by the type of regimen is equivocal, due to inaccurate classification. This in turn generates a variety of inconclusive trends that cannot be relied upon for clinical decision making. In conclusion, the present invention undisputably identifies a specific group of breast cancer patients who respond favorably to docetaxel but not to vinorelbine, thus showing predictive power for luminal B tumors in this particular setting. This is a very important property for a diagnostic assay, given that, as was shown in the FinHER clinical trial, docetaxel is more commonly associated with adverse effects than vinorelbinea, a fact that necessitated a reduction of the scheduled starting dose.

Therefore, the present invention can be used to assist in proper allocation of treatments in breast cancer. In particular, as shown for the first time in the context of a randomized clinical trial, breast cancer subtying by RT-qPCR allows to limit docetaxel-containing regimens to patients bearing luminal B tumors, which are more responsive to docetaxel treatment, and to consider alternative chemotherapeutics for patients with other tumor subtypes.

Example 5

Comparison of RT-qPCR and Conventional IHC Staining in Terms of Their Sensitivity Towards Ki67

A considerable number of cases (16.58%) are Ki67 negative by IHC, but are Ki67 positive by RT-qPCR. This demonstrates the higher sensitivity and robustness of the mRNA determination by the present invention as compared to the protein-based assessment of the prior art. In part, this may be due to multiple technical limitations of the IHC-based method (e.g., lack of protein preservation due to fixation and/or antigen retrieval issues, analysis time after tissue cutting, etc.) or staining interpretation problems (e.g., interpretation of faint nuclei stains).

Figure 20:
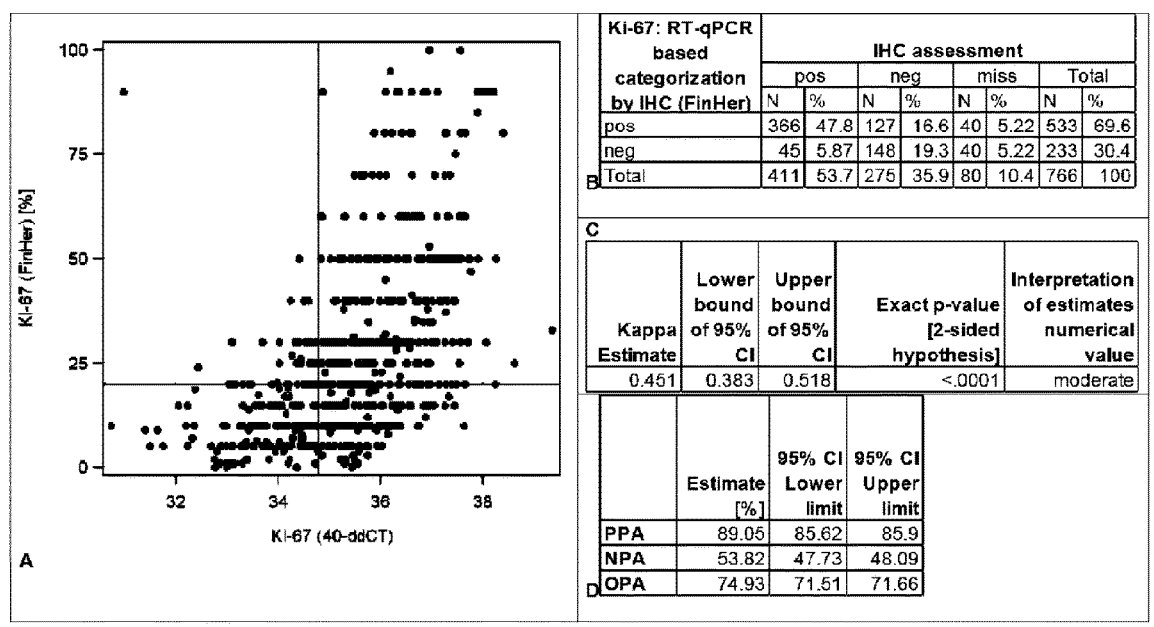

Due to the higher sensitivity of the RNA-based assessment of Ki67 by RT-qPCR, the concordance with IHC assessment of Ki67 is only moderate (see FIGS. 20 A, C). Moreover, this results in a low NPA for the present invention (53.82%), when local IHC assessment is used as reference method (FIG. 20D). By contrast the PPA is high, as RT-qPCR identifies the majority of positive IHC cases (94.2%). In conclusion, both methods significantly correlate ($p<0.0001$), but are only moderately concordant.

Table 8 is a contingency table displaying interrelations between RT-qPCR-based and IHC-based subtypes in the FinHer study population, wherein N is the number of observations, % (cell) is the overall frequency of the 16 potential subtype combinations, % (col.) is the distribution of RT-qPCR subtypes within IHC subtypes, and % (row) is the distribution of IHC subtypes within subtypes defined by the present application. Setting IHC subtypes as a "reference standard", concordance is highest for TNBCs (85.71%) and HER2-positives (79.43%) and lowest for luminal A (65.38%) and luminal B (61.22%) tumors.

TABLE 8

Interrelations between RT-qPCR-based and ICH-based subtypes in the FinHer study population.

| | | Tumor material subtype (RT-qPCR) | | | | | | | | | | | |
|---|---|---|---|---|---|---|---|---|---|---|---|---|---|
| | | HER2+ | | | | Luminal-A | | | | Luminal-B | | | |
| Tumor material subtype crosstabulation | | N | % (cell) | % (col.) | % (row) | N | % (cell) | % (col.) | % (row) | N | % (cell) | % (col.) | % (row) |
| Tumor material subtype (FinHer) | HER2+ | 139 | 19.41 | 79.43 | 85.28 | 5 | 0.70 | 3.21 | 3.07 | 12 | 1.68 | 4.08 | 7.36 |
| | Luminal-A | 12 | 1.68 | 6.86 | 6.35 | 102 | 14.25 | 65.38 | 53.97 | 75 | 10.47 | 25.51 | 39.68 |
| | Luminal-B | 17 | 2.37 | 9.71 | 6.77 | 48 | 6.70 | 30.77 | 19.12 | 180 | 25.14 | 61.22 | 71.71 |
| | Triple Negative | 7 | 0.98 | 4.00 | 6.19 | 1 | 0.14 | 0.64 | 0.88 | 27 | 3.77 | 9.18 | 23.89 |
| | Total | 175 | 24.44 | 100.00 | 24.44 | 156 | 21.79 | 100.00 | 21.79 | 294 | 41.06 | 100.00 | 41.06 |

| | | Tumor material subtype (RT-qPCR) | | | | | | |
|---|---|---|---|---|---|---|---|---|
| | | Triple Negative | | | | Total | | |
| Tumor material subtype crosstabulation | | N | % (cell) | % (col.) | % (row) | N | % (cell) | % (col.) | % (row) |
| Tumor material subtype (FinHer) | HER2+ | 7 | 0.98 | 7.69 | 4.29 | 163 | 22.77 | 22.77 | 100.00 |
| | Luminal-A | 0 | 0.00 | 0.00 | 0.00 | 189 | 26.40 | 26.40 | 100.00 |
| | Luminal-B | 6 | 0.84 | 6.59 | 2.39 | 251 | 35.06 | 35.06 | 100.00 |
| | Triple Negative | 78 | 10.89 | 85.71 | 69.03 | 113 | 15.78 | 15.78 | 100.00 |
| | Total | 91 | 12.71 | 100.00 | 12.71 | 716 | 100.00 | 100.00 | 100.00 |

Example 6

RT-qPCR- and IHC-based Subtyping Mainly Differ in Luminal B Assessment

The higher sensitivity of the RT-qPCR-based assessment of Ki67 results in a substantial difference in determining luminal A and luminal B patients, when compared to IHC-based assessment, while using the same algorithm to combine ESR1, PGR, HER2 and Ki67 for subtyping.

Of the 189 breast cancer patients that were classified as being luminal A by IHC methods, only 53.97% were also classified as being luminal A by RT-qPCR, while 39.68% turned out to be luminal B patients. In contrast, only 6.35% were reclassified as being HER2-positive and 0% turned out to be triple-negative. Moreover, of the 251 patients that were classified as being luminal B by IHC methods, 71.71% were also classified as being luminal B by RT-qPCR, while 19.12% turned out to be luminal A patients. In contrast, 6.77% were reclassified as being HER2-positive and 2.39% turned out to be triple-negative. Conversely, only 61.22% of the tumors that were classified as being luminal B by RT-qPCR were also classified by conventional IHC as being luminal B.

These data illustrate the modest concordance observed between the two assays for determining docetaxel-sensitive luminal B tumors, which is mainly caused by the limited sensitivity and/or robustness of the semi-quantitative assessment of Ki67 by IHC.

Example 7

High Ki67 Determined by RT-qPCR, but Low Ki67 Determined by IHC are Associated with Higher Risk of Distant Metastasis The approach of the present invention proves to have additional discriminatory power when considering a population comprising only ER-positive cases as determined by IHC. In this case, Ki67 was found to be discordant between the IHC- and RT-qPCR-based assays. As the determination of Ki67 by RT-qPCR and IHC was concordant in 514 out of 686 available data sets (74.92%), the number of samples for proving superiority of the mRNA based assessment is limited (n=172).

However, despite the small number of samples, Ki67 positivity by RT-qPCR indicates an increased risk for developing distant metastases in discordant cases. As shown in FIG. 21A, at 5 years follow-up 5% of ER-positive patients with low Ki67 mRNA expression developed distant metastasis, while 15% of patients exhibiting high Ki67 mRNA expression suffered distant metastasis (HR 3.315). This trend was unaffected by multivariate analysis (FIG. 21B).

This demonstrates that the higher sensitivity with respect to Ki67 assessment of the approach of the present invention provides additional prognostic information as compared to conventional IHC staining.

The invention claimed is:

1. A method of treating a breast cancer patient with adjuvant chemotherapy, said method comprising the steps:
   (a) obtaining or having obtained a biological sample of a breast tumor from the breast cancer patient;
   (b) performing an in vitro method on the biological sample, wherein the in vitro method identifies the patient as having a luminal B molecular subtype of the tumor, wherein the in vitro method comprises the steps:
      (i) determining the expression level of RNA transcript of human epidermal growth factor receptor 2 (HER2) in the biological sample of the breast tumor;
      (ii) determining the expression level of RNA transcript of estrogen receptor (ESR1) in the biological sample of the breast tumor;
      (iii) determining the expression level of RNA transcript of progesterone receptor (PGR) in the biological sample of the breast tumor; and
      (iv) determining the expression level of RNA transcript of proliferation antigen Ki-67 (Ki67) in the biological sample of the breast tumor,
   wherein no expression of RNA transcript of a gene other than HER2, ESR1, PGR and Ki67 is determined; and optionally, wherein the expression level of HER2, ESR1, PGR and Ki67 is normalized against the (mean) expression level of one or more reference genes in the sample of the tumor; and
   (c) providing adjuvant chemotherapy to the breast cancer patient.

2. The method of claim 1, wherein determining the expression level of RNA transcript of HER2, ESR1, PGR and Ki67 comprises determining whether the expression level of RNA transcript of HER2, ESR1, PGR and Ki67 is lower or higher than a defined expression threshold of RNA transcript of HER2, ESR1, PGR and Ki67.

3. The method of claim 1, wherein step (i) is performed before steps (ii), (iii) and (iv).

4. The method of claim 1, wherein step (iv) is performed after steps (i), (ii) and (iii).

5. The method of claim 1, wherein step (i) is performed before step (ii), step (ii) is performed before step (iii), and step (iii) is performed before step (iv).

6. The method of claim 1, wherein
an expression level of RNA transcript of HER2 which is lower than a defined expression threshold of RNA transcript of HER2;
an expression level of RNA transcript of ESR1 which is higher than a defined expression threshold of RNA transcript of ESR1;
an expression level of RNA transcript of PGR which is higher than a defined expression threshold of RNA transcript of PGR; and
an expression level of RNA transcript of Ki67 which is higher than a defined expression threshold of RNA transcript of Ki67
identify the molecular subtype of the tumor as luminal B.

7. The method of claim 1, wherein
an expression level of RNA transcript of HER2 which is lower than a defined expression threshold of RNA transcript of HER2;
an expression level of RNA transcript of ESR1 which is higher than a defined expression threshold of RNA transcript of ESR1;
an expression level of RNA transcript of PGR which is lower than a defined expression threshold of RNA transcript of PGR; and
an expression level of RNA transcript of Ki67 which is lower or higher than a defined expression threshold of RNA transcript of Ki67
identify the molecular subtype of the tumor as luminal B.

8. The method of claim 1, wherein
an expression level of RNA transcript of HER2 which is lower than a defined expression threshold of RNA transcript of HER2;
an expression level of RNA transcript of ESR1 which is lower than a defined expression threshold of RNA transcript of ESR1;
an expression level of RNA transcript of PGR which is higher than a defined expression threshold of RNA transcript of PGR; and
an expression level of RNA transcript of Ki67 which is higher than a defined expression threshold of RNA transcript of Ki67
identify the molecular subtype of the tumor as luminal B.

9. The method of claim 1, wherein
an expression level of RNA transcript of HER2 which is lower than a defined expression threshold of RNA transcript of HER2;
an expression level of RNA transcript of ESR1 which is higher than a defined expression threshold of RNA transcript of ESR1;
an expression level of RNA transcript of PGR which is lower than a defined expression threshold of RNA transcript of PGR; and
an expression level of RNA transcript of Ki67 which is higher than a defined expression threshold of RNA transcript of Ki67
identify the molecular subtype of the tumor as luminal B.

10. The method of claim 1, wherein the tumor is a solid tumor.

11. The method of claim 1, wherein the sample is RNA extracted from the tumor.

12. The method of claim 1, wherein the expression level of RNA transcript is determined by reverse transcription (RT) quantitative PCR.

13. The method of claim 12, wherein the quantitative PCR is fluorescence-based quantitative real-time PCR.

14. The method of claim 12, wherein the expression level of the RNA transcript is determined using ESR1-specific primers having a length of 15 to 30 nucleotides and comprising at least 10 contiguous nucleotides of the sequences of SEQ ID NOs: 1 and 2, and/or HER2-specific primers having a length of 15 to 30 nucleotides and comprising at least 10 contiguous nucleotides of the sequences of SEQ ID NOs: 4 and 5, and/or Ki67-specific primers having a length of 15 to 30 nucleotides and comprising at least 10 contiguous nucleotides of the sequences of SEQ ID NOs: 7 and 8, and/or PGR-specific primers having a length of 15 to 30 nucleotides and comprising at least 10 contiguous nucleotides of the sequences of SEQ ID NOs: 10 and 11.

15. The method of claim 12, wherein the expression level of the RNA transcript is determined using an ESR1-specific probe having a length of 20 to 35 nucleotides and comprising at least 15 contiguous nucleotides of the sequence of SEQ ID NO: 3, and/or a HER2-specific probe having a length of 20 to 35 nucleotides and comprising at least 15 contiguous nucleotides of the sequence of SEQ ID NO: 6, and/or a Ki67-specific probe having a length of 20 to 35 nucleotides and comprising at least 15 contiguous nucleotides of the sequence of SEQ ID NO: 9, and/or a PGR-specific probe having a length of 20 to 35 nucleotides and comprising at least 15 contiguous nucleotides of the sequence of SEQ ID NO: 12.

16. The method of claim 1, wherein the one or more reference genes are selected from the group comprising CALM2, B2M, RPL37A, GUSB, HPRT1 and GAPDH.

17. The method of claim 1, wherein the adjuvant chemotherapy comprises administration of a taxane.

18. The method of claim 17, wherein the taxane is docetaxel.

* * * * *

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: ESR_F

<400> SEQUENCE: 1
agagggtgcc aggctttgt                                                   19

<210> SEQ ID NO 2
<211> LENGTH: 22
<212> TYPE: DNA
<213> ORGANISM: Artificial Sequence
<220> FEATURE:
<223> OTHER INFORMATION: ESR_R

<400> SEQUENCE: 2
aggatctcta gccaggcaca tt                                               22

<210> SEQ ID NO 3
<211> LENGTH: 27
<212> TYPE: DNA
<213> ORGANISM: Artificial Sequence
<220> FEATURE:
<223> OTHER INFORMATION: ESR_P

<400> SEQUENCE: 3
tttgaccctc catgatcagg tccacct                                          27

<210> SEQ ID NO 4
<211> LENGTH: 21
<212> TYPE: DNA
```

```
<213> ORGANISM: Artificial Sequence
<220> FEATURE:
<223> OTHER INFORMATION: HER2_F

<400> SEQUENCE: 4
gaactcacct acctgcccac c                                              21

<210> SEQ ID NO 5
<211> LENGTH: 21
<212> TYPE: DNA
<213> ORGANISM: Artificial Sequence
<220> FEATURE:
<223> OTHER INFORMATION: HER2_R

<400> SEQUENCE: 5
gacctgcctc acttggttgt g                                              21

<210> SEQ ID NO 6
<211> LENGTH: 22
<212> TYPE: DNA
<213> ORGANISM: Artificial Sequence
<220> FEATURE:
<223> OTHER INFORMATION: HER2_P

<400> SEQUENCE: 6
ccaggaggtg cagggctacg tg                                             22

<210> SEQ ID NO 7
<211> LENGTH: 22
<212> TYPE: DNA
<213> ORGANISM: Artificial Sequence
<220> FEATURE:
<223> OTHER INFORMATION: KI67_F

<400> SEQUENCE: 7
cgagacgcct ggttactatc aa                                             22

<210> SEQ ID NO 8
<211> LENGTH: 25
<212> TYPE: DNA
<213> ORGANISM: Artificial Sequence
<220> FEATURE:
<223> OTHER INFORMATION: KI67_R

<400> SEQUENCE: 8
ggatacggat gtcacattca atacc                                          25

<210> SEQ ID NO 9
<211> LENGTH: 23
<212> TYPE: DNA
<213> ORGANISM: Artificial Sequence
<220> FEATURE:
<223> OTHER INFORMATION: KI67_P

<400> SEQUENCE: 9
acggtcccca ctttcccctg agc                                            23

<210> SEQ ID NO 10
<211> LENGTH: 27
<212> TYPE: DNA
<213> ORGANISM: Artificial Sequence
<220> FEATURE:
<223> OTHER INFORMATION: PGR_F

<400> SEQUENCE: 10
aaacttcttg ataacttgca tgatctt                                        27
```

```
<210> SEQ ID NO 11
<211> LENGTH: 25
<212> TYPE: DNA
<213> ORGANISM: Artificial Sequence
<220> FEATURE:
<223> OTHER INFORMATION: PGR_R

<400> SEQUENCE: 11
caataacttc agacatcatt tctgg                                           25

<210> SEQ ID NO 12
<211> LENGTH: 30
<212> TYPE: DNA
<213> ORGANISM: Artificial Sequence
<220> FEATURE:
<223> OTHER INFORMATION: PGR_P

<400> SEQUENCE: 12
cgggactgga taaatgtatt caagcagtac                                      30

<210> SEQ ID NO 13
<211> LENGTH: 22
<212> TYPE: DNA
<213> ORGANISM: Artificial Sequence
<220> FEATURE:
<223> OTHER INFORMATION: RAC_F

<400> SEQUENCE: 13
gaatgtgcgg aatctgtttg ag                                              22

<210> SEQ ID NO 14
<211> LENGTH: 21
<212> TYPE: DNA
<213> ORGANISM: Artificial Sequence
<220> FEATURE:
<223> OTHER INFORMATION: RAC_R

<400> SEQUENCE: 14
tcgccaactg gataaattgg a                                               21

<210> SEQ ID NO 15
<211> LENGTH: 23
<212> TYPE: DNA
<213> ORGANISM: Artificial Sequence
<220> FEATURE:
<223> OTHER INFORMATION: RAC_P

<400> SEQUENCE: 15
actgagaatc tccacccggc gca                                             23

<210> SEQ ID NO 16
<211> LENGTH: 20
<212> TYPE: DNA
<213> ORGANISM: Artificial Sequence
<220> FEATURE:
<223> OTHER INFORMATION: B2M_F

<400> SEQUENCE: 16
gtatgcctgc cgtgtgaacc                                                 20

<210> SEQ ID NO 17
<211> LENGTH: 22
<212> TYPE: DNA
<213> ORGANISM: Artificial Sequence
<220> FEATURE:
```

```
<223> OTHER INFORMATION: B2M_R

<400> SEQUENCE: 17
ggcatcttca aacctccatg at                                           22

<210> SEQ ID NO 18
<211> LENGTH: 25
<212> TYPE: DNA
<213> ORGANISM: Artificial Sequence
<220> FEATURE:
<223> OTHER INFORMATION: B2M_P

<400> SEQUENCE: 18
agtgggatcg agacatgtaa gcagc                                        25

<210> SEQ ID NO 19
<211> LENGTH: 19
<212> TYPE: DNA
<213> ORGANISM: Artificial Sequence
<220> FEATURE:
<223> OTHER INFORMATION: CALM2_F

<400> SEQUENCE: 19
aggaggcgaa ttagtccga                                               19

<210> SEQ ID NO 20
<211> LENGTH: 20
<212> TYPE: DNA
<213> ORGANISM: Artificial Sequence
<220> FEATURE:
<223> OTHER INFORMATION: CALM2_R

<400> SEQUENCE: 20
gctcttcagt cagttggtca                                              20

<210> SEQ ID NO 21
<211> LENGTH: 22
<212> TYPE: DNA
<213> ORGANISM: Artificial Sequence
<220> FEATURE:
<223> OTHER INFORMATION: CALM2_P

<400> SEQUENCE: 21
tcgcgtctcg gaaaccggta gc                                           22
```